US011634557B2

(12) United States Patent
Appel et al.

(10) Patent No.: US 11,634,557 B2
(45) Date of Patent: Apr. 25, 2023

(54) BIOMIMETIC, MOLDABLE, SELF-ASSEMBLED CELLULOSE SILICA-BASED TRIMERIC HYDROGELS AND THEIR USE AS VISCOSITY MODIFYING CARRIERS IN INDUSTRIAL APPLICATIONS

(71) Applicant: THE BOARD OF TRUSTEES OF THE LELAND STANFORD JUNIOR UNIVERSITY, Stanford, CA (US)

(72) Inventors: Eric A. Appel, Palo Alto, CA (US); Anthony C Yu, Stanford, CA (US)

(73) Assignee: THE BOARD OF TRUSTEES OF THE LELAND STANFORD JUNIOR UNIVERSITY, Stanford, CA (US)

( * ) Notice: Subject to any disclaimer, the term of this patent is extended or adjusted under 35 U.S.C. 154(b) by 0 days.

(21) Appl. No.: 16/709,832

(22) Filed: Dec. 10, 2019

(65) Prior Publication Data
US 2020/0109253 A1    Apr. 9, 2020

Related U.S. Application Data

(62) Division of application No. 15/716,500, filed on Sep. 26, 2017, now Pat. No. 10,590,257.

(60) Provisional application No. 62/399,664, filed on Sep. 26, 2016.

(51) Int. Cl.
| | |
|---|---|
| C08K 3/36 | (2006.01) |
| A61K 47/02 | (2006.01) |
| A61K 47/38 | (2006.01) |
| A61L 27/52 | (2006.01) |
| C09K 21/02 | (2006.01) |
| C09K 21/14 | (2006.01) |
| A61L 27/02 | (2006.01) |
| A61L 27/20 | (2006.01) |
| A61K 9/06 | (2006.01) |
| A01N 25/04 | (2006.01) |
| B08B 9/032 | (2006.01) |
| A01N 25/10 | (2006.01) |
| C08L 1/28 | (2006.01) |
| A62D 1/00 | (2006.01) |

(52) U.S. Cl.
CPC .............. *C08K 3/36* (2013.01); *A01N 25/04* (2013.01); *A01N 25/10* (2013.01); *A61K 9/06* (2013.01); *A61K 47/02* (2013.01); *A61K 47/38* (2013.01); *A61L 27/025* (2013.01); *A61L 27/20* (2013.01); *A61L 27/52* (2013.01); *A62D 1/0064* (2013.01); *B08B 9/0321* (2013.01); *C08L 1/28* (2013.01); *C08L 1/284* (2013.01); *C09K 21/02* (2013.01); *C09K 21/14* (2013.01); *A61L 2400/12* (2013.01); *C08K 2201/011* (2013.01); *C08L 2666/58* (2013.01)

(58) Field of Classification Search
CPC ..... A62D 1/0064; A61L 27/025; A61L 27/20; A61L 27/52; A61L 2400/12; A61K 9/06; A61K 47/38; A61K 47/02; C08L 1/284; C08L 1/28; C08L 2666/58; C08K 3/36; C08K 2201/011; C09K 21/01; C09K 21/14
See application file for complete search history.

(56) References Cited

U.S. PATENT DOCUMENTS

| | | | |
|---|---|---|---|
| 4,192,727 A ‡ | 3/1980 | Ward | A61L 15/60 521/137 |
| 5,143,724 A ‡ | 9/1992 | Leshchiner et al. | |
| 5,410,016 A ‡ | 4/1995 | Hubbell et al. | |
| 5,480,436 A ‡ | 1/1996 | Bakker et al. | |
| 5,785,993 A ‡ | 7/1998 | Baker et al. | |
| 5,888,988 A ‡ | 3/1999 | Elson | |
| 6,150,581 A ‡ | 11/2000 | Jiang et al. | |
| 6,673,093 B1 ‡ | 1/2004 | Sawhney | |
| 6,818,018 B1 ‡ | 11/2004 | Sawhney | |
| 7,125,860 B1 ‡ | 10/2006 | Renier et al. | |
| 7,347,850 B2 ‡ | 3/2008 | Sawhney | |
| 8,455,001 B2 ‡ | 6/2013 | Ito et al. | |
| 8,709,450 B2 ‡ | 4/2014 | Kaneko et al. | |
| 8,728,524 B2 ‡ | 5/2014 | Bellini et al. | |
| 8,748,409 B2 ‡ | 6/2014 | Kaneko et al. | |
| 8,778,326 B2 ‡ | 7/2014 | Lu et al. | |
| 8,859,523 B2 ‡ | 10/2014 | Prestwich et al. | |
| 8,916,143 B2 ‡ | 12/2014 | Putnam et al. | |
| 9,089,730 B2 * | 7/2015 | Shalev | A62D 1/005 |
| 9,289,279 B2 ‡ | 3/2016 | Wilson et al. | |
| 10,590,257 B2 * | 3/2020 | Appel | C09K 21/14 |
| 2003/0180251 A1 ‡ | 9/2003 | Friedrich | A61L 31/048 424/78 |

(Continued)

FOREIGN PATENT DOCUMENTS

| | | | |
|---|---|---|---|
| EP | 2511336 B1 | | 10/2012 |
| EP | 2511336 B1 | ‡ | 10/2012 |

(Continued)

OTHER PUBLICATIONS

Bourges et al., Advances in Colloid and Interface Science, 99, 215-218. (Year: 2002).‡
Artivashist et al., Oriental Journal of Chemistry, 29(3) pp. 861-870. (Year: 2013).‡
Appel et al., Nature Materials, vol. 13, pp. 231-232. (Year: 2014).‡
Appel et al.; Activation energies control the macroscopic properties of physically cross-linked materials; Angew. Chem. Ind. Ed.; 53; 7 pgs.; Sep. 15, 2014.
Appel et al.; Exploiting electrostatic interactions in polymer-nanoparticle hydrogels; ACS Macro letters; 4(8); pp. 848-852; Jul. 27, 2015.

(Continued)

*Primary Examiner* — Abigail Vanhorn
(74) *Attorney, Agent, or Firm* — Rimon Law PC

(57) ABSTRACT

The present invention provides moldable, fully scalable cellulose silica-based hydrogels for use as low-cost and safe carriers and aqueous viscosity modifiers in various industrial and medical applications.

8 Claims, 17 Drawing Sheets

(56) References Cited

U.S. PATENT DOCUMENTS

| | | | |
|---|---|---|---|
| 2004/0023842 A1‡ | 2/2004 | Pathak et al. | |
| 2005/0271727 A1‡ | 12/2005 | Yao | |
| 2006/0177481 A1‡ | 8/2006 | Sawhney | A61K 9/0024 424/42 |
| 2007/0001156 A1‡ | 1/2007 | Toreki | A62D 1/0064 252/601 |
| 2008/0069857 A1‡ | 3/2008 | Yeo | A61L 31/041 424/42 |
| 2008/0107703 A1‡ | 5/2008 | Tabata | A61K 9/0014 424/42 |
| 2009/0294049 A1‡ | 12/2009 | Udipi | A61L 24/0031 156/27 |
| 2010/0285113 A1‡ | 11/2010 | Shoichet | A61K 9/0024 424/45 |
| 2010/0291055 A1‡ | 11/2010 | Athanasiadis et al. | |
| 2011/0178184 A1‡ | 7/2011 | Kaneko | A61K 9/0024 514/77 |
| 2012/0298777 A1 | 11/2012 | Holladay et al. | |
| 2015/0202299 A1‡ | 7/2015 | Burdick | A61L 31/042 424/85 |
| 2016/0030789 A1* | 2/2016 | Cordani | A62D 1/0014 252/2 |
| 2016/0228601 A1‡ | 8/2016 | He | A61K 9/0024 |
| 2016/0287745 A1‡ | 10/2016 | Grinstaff et al. | |
| 2017/0196818 A1 | 7/2017 | Shin et al. | |
| 2017/0319506 A1‡ | 11/2017 | Appel | A61K 9/06 |
| 2017/0362380 A1‡ | 12/2017 | Christman et al. | |
| 2018/0086896 A1 | 3/2018 | Appel et al. | |
| 2018/0280586 A1‡ | 10/2018 | Appel et al. | |

FOREIGN PATENT DOCUMENTS

| | | | | |
|---|---|---|---|---|
| KR | 20060011503 A | ‡ | 2/2006 | |
| KR | 20170110882 A | ‡ | 10/2017 | |
| WO | WO93/017669 A1 | | 9/1993 | |
| WO | WO1993017669 A1 | ‡ | 9/1993 | |
| WO | WO03/084481 A2 | ‡ | 10/2003 | |
| WO | WO03/084481 A2 | | 10/2003 | |
| WO | WO2005/110377 A1 | ‡ | 11/2005 | |
| WO | WO2013/076305 A1 | ‡ | 5/2013 | |
| WO | WO2013/124654 A1 | ‡ | 8/2013 | |
| WO | WO2014/116187 A1 | ‡ | 7/2014 | |
| WO | WO2014/125418 A1 | | 8/2014 | |
| WO | WO-2014125418 A1 | ‡ | 8/2014 | A61F 13/0209 |
| WO | WO2015/172073 A1 | ‡ | 11/2015 | |
| WO | WO 2016/049360 A1 | ‡ | 3/2016 | |
| WO | WO2016/049360 A1 | | 3/2016 | |
| WO | WO2016049360 A1 | ‡ | 3/2016 | |

OTHER PUBLICATIONS

Appel et al.; Formation of single-chain polymer nanoparticles in water through host-guest interactions; Angew. Chem. Int. Ed.; 51; pp. 4185-4189; Apr. 23, 2012.

Appel et al.; Gluing Gels: A nanoparticle solution; Nature Materials; 13(3): pp. 231-232; Mar. 2014.

Appel et al.; High-water-content hydrogels from renewable resources through host-guest interactions; J. Am. Chem. Soc.; 134(28); pp. 11767-11773; Jul. 18, 2012.

Appel et al.; Self-assembled hydrogels utilizing polymer-nanoparticle intersctions; Nature Communicationss; 6; pp. 6295; doi: 10:1038/ncomms7295; 19 pages; (Author Manuscccript); Feb. 19, 2015.

Appel et al.; Supramolecular cross-linked metworks via host-guest complexation with cucurbit[8] uril; Journal of the American Chemical Society; 132(40); pp. 14251-14260; Sep. 16, 2010.

Appel et al.; Supramolecular polymeric hydrogels; Chemical Society Reviews; 41(18); pp. 6195-6214; Sep. 2012.

Appel et al.; Sustained release of proteins from high water content supramolecular polymer hydrogels; Biomaterials; 33(18); pp. 4646-4652; Jun. 1, 2012.

Appel et al.; The control of cargo release from physically cross-linked hydrogels by crosslink dynamics; Biomateriais; 35(37); pp. 9897-9903; Dec. 1, 2014.

Artivashist et al.; Hydrogels: Smart materials for drug delivery; Oriental Journal of Chemistry; 29(3); pp. 861-870; Nov. 5, 2013.

Bang et al.; Injectable pullulan hydrogel for the prevention of postoperative tissue adhesion; International Journal of Biological Macromolecules; 87; pp. 155-162; Jun. 2016.

Bao et al.; Swelling behaviors of organic/inorganic composites based on various cellulose derivatives and inorganic particles; Carbohydrate Polymers; 88(2); pp. 589-595; Apr. 2012.

Bremer et al.; Laboratory scale clean-in-place (CIP) studies on the effectiveness of different caustic and acid wash steps on the removal of dairy biofilms; Intl. J. of Food Microb.; 106(3); pp. 254-262; Feb. 15, 2006.

Bourges et al.; Synthesis and General Properties of Silated-Hydroxypropyl Methylcellulose in Prospect of Biomedical Use; Advances in Colloid and Interface Science; 99 (3), pp. 215-228; Dec. 2, 2002.

Drevelle et al.; Thermal and fire behaviour of ammonium polyphosphate/ acrylic coated cotton/PESFR fabric; Polymer Degradation and Stability; 88(1); pp. 130-137; Apr. 1, 2005.

Ehrbar et al.; Drug-sensing hydrogels for the inducible release of biopharmaceuticals; Nature materials; 7(10); pp. 800-804; Oct. 2008.

Evans et al.; Investigation into the transportation and melting of thick ice slurries in pipes; Intl. Journal of Refrig.; 31(1); pp. 145-151; Jan. 1, 2008.

Fu et al; Biodegradable and thermosensitive monomethoxy poly-(ethylene glycol)-poly(lactic acid) hydrogel as a barrier for prevention of post-operative abdominal adhesion; Journal of Biomedical Nanotechnology; 10(3); pp. 427-436; Mar. 2014.

Gesan-Guiziou et al.; Nanofiltration for the recovery of caustic cleaning-in-place solutions: robustness towards large variations of composition; Journal of Dairy Research; 69(4): pp. 633-643: Nov. 2002.

Gimenez et al.; Long-term forest fire retardants: a review of quality, effectiveness, application and environmental considerations; Intl. J. of Wildland Fire; 13(1); pp. 1-15; Apr. 27, 2004.

Gu et al.; Study on preparation and fire-retardant mechanism analysis of intumescent flame-retardant coatings; Surface and coatings tech.; 201(18); pp. 7835-7841; Jun. 25, 2007.

Hales et al.; Ice fraction measurement of ice slurries through electromagnetic attenuation; Intl. J. of Refrig.; 47; pp. 98-104; Nov. 1, 2014.

Harada et al.; Macroscopic self-assembly through molecular recognition; Nature Chem.; 3(1); pp. 34-37; Jan. 2011.

Hoare et al.; Prevention of peritoneal adhesions using polymeric rheological blends; Acta Biomaterialia; 10(3); pp. 1187-1193; 16 pages; (Author Manuscript); Mar. 2014.

Hu et al.; Detection of poly- and parflucroalkyl substances (PFASs) in U.S. drinking water inked to industrial sites, milltary fire training areas, and wastewater treatment plants; Env. Sci. and Tech. Letters; 3(10); pp. 344-350: Aug. 9, 2016.

Ishiyama et al.; The prevention of peritendinous adhesions by phospholipid polymer hydrogel formed in situ by spontaneous intermolecular interactions; Biomaterials; 31(14); pp. 4009-4016; May 2010.

Kapsabelis et al.; Adsorption of ethyl (hydroxyethyl) cellulose onto silica particles: the role of surface chemistry end temperature; J. of colloid and interface sci.; 228(2): pp. 297-305; Aug. 15, 2000.

Karacam et al.; Prevention of pleural adhesions using a membrane containing polyethylene glycol in rats; International Journal of Medical Sciences; 8(5); pp. 380-386: (year of pub. sufficiently earlier than effective US filing date and any foreign priority date): 2011.

Krielen et al.; In-hospital costs of an admission for adhesive small bowel obstruction; World Journal of Emergency Surgery; 11(1); pp. 49; DOI 10.1186/s13017-016-0109-y; 8 pages; Dec. 2016.

Krishna et al.; Protein- and oeptide-modified synthetic polymeric biomaterials; Peptide Science: Original Res. On Biomolecules; 94(1); pp. 32-48; Jan. 20, 2010.

(56) References Cited

OTHER PUBLICATIONS

Lu et al.; Injectable shear-thinning hydrogels engineered with a self-assembled dock-and-lock mechanism; Biomateriais; 33(7): pp. 2145-2153; Mar. 2012.
Maupin et al.; Estimated use of water in the United States in 2010; USGS Survey (No. 1405); 64 pgs.; (year of pub. sufficiently earlier than effective US filing date and any foreign priority date) 2014.
Merin et al.; Cleaning-in-place in the dairy industry: criteria for reuse of caustic (NaOH) solutions; Le Lait; 82(3); pp. 357-366; May 1, 2002.
Moody et al.. Monitoring perfluorinated surfactants in blota and surface water samples following an accidental release oi firefighting foam into Etoblcoke Creek; Environ. Sci. and Tech.; 36(4); pp. 545-551; Feb. 15, 2002.
Moody et al; Occurrence and persistence of perfluoroctanesulfonate and other perfluorinated surfactants in groundwater at a fire-training area at Wurtsmith Air Force Base, Michigan, USA; J. Environ. Mon.; 5(2); pp. 341-345; Mar. 10, 2003.
Moody et al.; Perfluorinated surfactants and the environmental implications of their use in fire-fighting foams; Environ. Sci. and Technol.; 34(18); pp. 3864-3870; Sep. 15, 2000.
Mulyasasmita et al.; Molecular-level engineering of protein physical hydrogels for predictive sol-gel phase behavior; Biomacromolecules; 12(10); pp. 3406-3411; Sep. 2, 2011.
Nakahata et al.; Redox-responsive self-healing materials formed from host-guest polymers; Nature Comm.; 2(511); pp. 1-6; Oct. 25, 2011.
Okabayashi et al; Adhesions after abdominal surgery: a systematic review of the incidence, distribution and severity; Surgery Today; 44(3); pp. 405-420; Mar. 1, 2014.
Osada et al.: The effect of cross-linked hyaluronate hydrogel on the reduction of post-surgical adhesion reformation in rabbits; Journal of International Medical Research; 5; pp. 233-241; Sep. 1999.
Parisi-Amon et al; Protein-engineered injectable hydrogel to improve retention of transplanted adipose-derived stem cells; Advanced Healthcare Materials; 2(3); pp. 428-432; 10 pages; (Author Manuscript); Mar. 2013.
Park et al.; In situ supramolecular assembly and modular modification of hyaluronic acid hydrogels for 3D cellular engineering; ACS Nano; 6(4); pp. 2960-2968; Mar. 15, 2012.
Patterson et al.; In situ characterization of the degradation of PLGA microspheres in hyaluronic acid hydrogels by optical coherence tomography; IEEE Transactions on Medical Imaging: vol. 28; pp. 74-81; Jan. 2009.
Petka et al.; Reversible hydrogels from self-assembling artifical proteins; Science; 281(5375); pp. 389-392; Jul. 17, 1998.
Pritchard et al.; An injectable thiol-acrylate poly(ethylene glycol) hydrogel for sustained release of methylprenisolone sodium succinate; Biomaterials; 32(2); pp. 587-597; 30 pages; (Author Manuscript): Jan. 2011.
Quarini; Ice-pigging to reduce and remove fouling and to achieve clean-in-place; Applied thermal Eng.; 22(7); pp. 747-753; May 1, 2002.
Quarini et al.; Investigation and development of an innovative pigging technique for the water-supply ndustry; Proc. Inst. Mech. Eng., Part E: J. Proc. Mech. Eng.; 224(2); pp. 79-89; May 1, 2010.
Rodell et al.; Rational design of network properties in guest-host assembled and shear-thinning hyaluronic acid hydrogels; Biomacromolecules; 14(11); pp. 4125-4134: 20 pages: (Author Manuscript): Oct. 14, 2013.
Rodell et al.; Shear-thinning supramolecular hydrogels with secondary autonomous covalent crosslinking to modulate viscoelastic properties in vivo; Adv. Functional Mat.; 25(4); pp. 636-644; Jan. 28. 2015.
Rose et al.; Nanoparticle solutions as adhesives for gels and biological tissues; Nature; 505(7483); pp. 382-385; Jan. 16, 2014.
Rowland et al.; Dynamically crosslinked materials via recognition of amino acids by cucurbit [8] uril; J. Mat. Chem. B; 1(23); pp. 2904-2910; Apr. 30, 2013.
Salem et al.; Porous polymer and cell composites that self-assemble in situ; Advanced Materials; 15(3); pp. 210-213; Feb. 5, 2003.
Schroeder; Can fire suppressant gels protect log decks. A case study to test the concept; Wildland Fire Operations Research Group; Vancouver; (year of pub. sufficiently earlier than effective US filing date and any (foreign priority date) 2005.
Schroeder; Can fire suppressant gels protect log decks? Part III—Two case studies to test gel effectiveness (against radiant and convective heat transfer; Vancouver; (year of pub. sufficiently earlier than effective US filing date and any foreign priority date) 2006.
Schroeder; Effectiveness of forest fuel management: a crown fire case study in the Northwest Territories, Canada; Forest Eng. Res. Inst. of Canada, Vancouver; (year of pub. sufficiently earlier than effective US fling date and any foreign priority date) 2006.
Shen et al.; Tuning the erosion rate of artifical protein hydrogels through control of network topology; Nature Materials; 5(2); pp. 153-158; Feb. 2006.
Song et al.; Peritoneal adhesion prevention with a biogradable and injectable N, O-carboxymethyl chitosan-aldehyde hyaluronic acid hydrogel in a rat repeated injury model; Scientific Reports; 6; doi: 10.1038/srep37600; 13 pages; Nov. 21, 2016.
Tamesue et al.; Linear versus dendritic molecular binders for hydrogel network formation with clay nanosheets: studies with ABA triblock copolyethers carrying guanidinium ion pendants; J. Am. Chem. Soc.; 135(41): pp. 15650-15655; Oct. 3, 2013.
Wang et al.; High-water-content mouldable hydrogels by mixing clay and a dendritic molecular binder; Natue 463(7279); pp. 339-343; Jan. 21, 2010.
Wang et al.; PLGA-chitosan/PLGA-aiginate nanoparticle blends as biodegradable colloidal gels for seeding human umbillical cord mesenchymal stem cells; Journal of Bionedical Research, Part A; 96(3); pp. 520-527; (Author Manuscript) Mar. 2011.
Webber et al.; Supramolecular biomateriais; Nature Materials; 15(1); pp. 13-26; Jan. 2016.
Wong Po Foo et al.; Two-component protein-engineered physical hydrogels for cell encapsulation; Proceedings of the National Academy of Sciences; 106(52); pp. 22067-22072; doi: 10.1073/pnas. 0904851106; 6 pages; Dec. 29, 2009.
Yamaguchi et al.; Photoswitchable gel assembly based on molecular recognition; Nature Comm.; 3(603); pp. 1-5; Jan. 3, 2012.
Yamaguchi et al.; Self-assembly of gels through molecular recognition of cyclodextrins: Shape selectivity for linear and cyclic guest molecules; Macromolecules; 44(8); pp. 2395-2399; Mar. 25, 2011.
Yeo et al.; Polymers in the prevention of peritoneal adhesions; European Journal of Pharaceutics and Biopharmaceutics; 68(1); pp. 57-66; 16 pages; (Author Manuscript); Jan. 2008.
Yu et al.; Comparative studies of thermogels in preventing postoperative adhesions and corresponding mechanisms; Biomater. Sci.; 2(8); pp. 1100-1109; doi: 10.1009/C4M0029C; retrieved from the internet (http://pubs.rsc.org/-/content/articlehtml/2014/bm/c4bm00029c); 30 pages; (year of pub. sufficiently earlier then effective US filing date and any foreign priority date) 2014.
Zhang et al.; Biodegradable and thermoreversible PCLA-PEG-PCLA hydrogel as a barrier for prevention of post-operative adhesion; Biomateriais; 32(21); pp. 4725-4736; Jul. 2011.
Zhu et al.; Metal and light tree "click" hydrogals for prevention of post-operative peritoneal adhesions; Polymer Chemistry; 5(6); pp. 2018-2026; (year of pub. sufficiently earlier than effective US filing date and any foreign priority dats) 2014.
Xu et al.; Genetically engineered block copolymers: influence of the length and structure of the coiled-coil blocks on hydrogel self-assembly; Pharm. Res.; 25(3); pp. 674-682; Mar. 1, 2008.
Xu et al.; Reversible hydrogels from self-assembling genetically engineered protein block copolymers; Biomacromolecules; 6(3); pp. 1739-1749; May 9, 2005.
Appeal et al.; U.S. Appl. No. 16/590,189 entitled "Adhesion prevention with shear-thinning polymeric hydrogels," filed Oct. 1, 2019.
Adusumilli et al.; Regional delivery of mesothelin-targeted car t cell therapy generates potent and long tasting cd4-dependent tumor immunity; Science Translational Medicine; 6(261); pp. 261ra151-261ra151; 31 pages; (Author Manuscript); Nov. 2014.

(56) References Cited

OTHER PUBLICATIONS

Anthony et al.; Scalable manufacturing of biomimetic moldable hydrogels for industrial applications; Porceedings National Academy Sciences; 113(50); pp. 14255-14260; Dec. 2016.

Chu et al.; A bright cyan-excitable orange fluorescent protein facilitates dual-emission microscopy and enhances bioluminescence imaging in vivo; Nature Biotechnology; 34(7); pp. 760-767; 29 pages; (Author Manuscript): Jul. 2016.

Conlon et al.; Redistribution, hyperproliferation, activation of natural killer cells and CD8 T cells, and cytokine production during first-in-human clinical trail of recombinant human interleukin-15 in patients with cancer; Journal of Clinical Oncology; 33(1); pp. 74-82; Jan. 2015.

Foster et al.; The diverse roles of hydrogel mechanics in injectable stem cell transplantation; Current Opinion Chemical Engineering; 15; pp. 15-23; 17 pages; (Author Manuscript); Feb. 2017.

Hall et al.; Engineered luciferase reporter from a deep sea shrimp utilizing a novel imidazopyrazinone substrate; ACS Chemical Biology; 7(11); pp. 1848-1857; Nov. 2012.

Hughes et al.; Transfer of a tcr gene derived from a patient with marked antitumor response conveys highly active t-cell effector functions; Human Gene Therapy; 16(4); pp. 457-472: 25 pages; (Author Manuscript); Apr. 2005.

Long et al.; 4-1BB costimulation ameliorates t cell exhaustion induced by tonic signaling of chimeric antigen receptors; Nature Medicine; 21(6); pp. 581-590; 27 pages; (Auhtor Manuscript); Jun. 2015.

Lotze et al.; Clinical effects and toxicity of interleukin-2 in patients with cancer; Cancer; 58(12); pp. 2764-2772; Dec. 1986.

Nair et al.; A simple practice guide for dose conversion between animals and human; Journal Basic Clinical Pharmacy; 7(2); pp. 27-31; Mar. 2016.

Ring et al.; Mechanistic and structural insight into the functional dichotomy between il-2 and il-15; Nature Immunology; 13(12); pp. 1187-1195; 26 pages; (Author Manuscript); Dec. 2012.

Shaner et al.; A bright monomeric green fluorescent protein derived from branchiostoma lanceolatum; Nature Methods; 10(5); pp. 407-409; 18 pages; (Author Manuscript); May 2013.

Smith et al.; Biopolymers codelivering engineered t cells and sting agonists can eliminate heterogeneous tumors; The Journal clinical Investigation; 127(6); pp. 2176-2191; Jun. 2017.

Sridhar et al.; Regional delivery of chimeric antigen receptor (car) t-cells for cancer therapy; Cancers; 9(7); pp. 92; 10 pages; doi:10.3390/cancers9070092; Jul. 2017.

Stephan et al.; Bipolymer implants enhance the efficacy of adoptive t-cell therapy; Nature Biotechnology; 33(1); pp. 97-101; 18 pages; (Author Manuscript); Jan. 2015.

Waldmann et al.; Safety (toxicity), pharmacokinetics, immunogenicity, and impact on elements of the normal immune system of recombinant human il-15 in rhesus macaques; Blood, The Journal American Society Hermatology; 117(18); pp. 4787-4795; May 2011.

Walker et al.; Tumor antigen and receptor densities regulate efficacy of a chimeric antigen receptor targeting anaplastic lymphoma kinase; Molecular Therapy; 25(9); pp. 2189-2201; Sep. 2017.

Agmon et al.; U.S. Appl. No. 17/281,014 entitled "Injectable hydrogels for controlled release of immunomodulatory compounds," filed Mar. 29, 2021.

Richards; Cancer immunotherapy gets assist from micro-scale engineering; 7 pages; retrieved from the internet (https://www.fredhutch.org/en/news/center-news/2019/12/stephan-thin-film-stent-immunotherapy.html) on Nov. 11, 2021.

\* cited by examiner
‡ imported from a related application

BIOMIMETIC, MOLDABLE, SELF-ASSEMBLED CELLULOSE SILICA-BASED TRIMERIC HYDROGELS AND THEIR USE AS VISCOSITY MODIFYING CARRIERS IN INDUSTRIAL APPLICATIONS

CROSS REFERENCE TO RELATED APPLICATIONS

This application is a continuation of U.S. patent application Ser. No. 15/716,500, filed on Sep. 26, 2017, titled "BIOMIMETIC, MOLDABLE, SELF-ASSEMBLED CELLULOSE SILICA-BASED TRIMERIC HYDROGELS AND THEIR USE AS VISCOSITY MODIFYING CARRIERS IN INDUSTRIAL APPLICATIONS," which claims priority and other benefits from U.S. Provisional Patent Application Ser. No. 62/399,664, filed Sep. 26, 2016, entitled "METHODS OF PRODUCING MOLDABLE HYDROGELS AND USES THEREOF," each of which is herein incorporated by reference in its entirety.

INCORPORATION BY REFERENCE

All publications and patent applications mentioned in this specification are incorporated herein by reference in their entirety to the same extent as if each individual publication or patent application was specifically and individually indicated to be incorporated by reference.

FIELD

The present invention relates to the field of self-assembled biopolymeric systems, and in particular to self-assembled cellulose silica-based biopolymeric systems that form moldable hydrogels that are useful to serve as aqueous viscosity modifying carriers in various industrial and medical applications.

BACKGROUND

Traditional, covalently cross-linked hydrogels which comprise a class of soft materials that bind and retain large amounts of water and exhibit broadly tunable mechanical properties have limited utility because their irreversible crosslinks do not allow for stimuli-responsive aqueous viscosity modification or the ability to rearrange their shape in response to applied stress (Appel et al., 2012a).

Recent advances in supramolecular chemistry and materials science have introduced moldable polymeric systems as unique solutions to many critical industrial challenges (Appel et al., 2012a; Rodell et al., 2015). Due to the exploitation of specific and tunable non-covalent interactions, moldable polymeric systems, in contrast to covalently cross-linked hydrogels, exhibit viscous flow under shear stress (shear-thinning) and rapid recovery when the applied stress is relaxed (self-healing) which allows for precise tuning of their flow properties to meet the engineering requirements for diverse applications, including injection, pumping, or spraying.

Although many industrial applications would benefit from moldable polymeric systems that facilitate administration by flow, injection, pumping or spraying, there is a recognized shortage of moldable polymeric systems that not only allow finely tunable control over their mechanical properties, but that can also be scaled up, and be produced cost-effectively and environmentally friendly.

It would be highly desirable to rationally engineer a scalable biopolymeric system that combines readily available, inexpensive and non-toxic components in such a way that they transiently and reversibly self-assemble and so allow control and adjustment to a variety of engineering requirements. The present invention addresses this need.

SUMMARY OF THE DISCLOSURE

Compositions and methods are provided relating to scalable, biomimetic, moldable, self-assembled biopolymeric systems that find use as aqueous viscosity modifying carriers in various industrial and medical applications including as carriers of fire retardants, fertilizers, pesticides, and pipeline cleaning agents. Primary embodiments of the invention include scalable, biomimetic, moldable, self-assembled cellulose silica-based trimeric hydrogels (CSG) formed with pairs of cellulose derivatives.

In various embodiments of the invention, colloidal silica nanoparticles form moldable hydrogels by selective, pH-dependent adsorption to paired biopolymers (cellulose derivatives) via multivalent and non-covalent interactions and crosslinking. This approach affords unique control over the flow properties of the cellulose silica-based hydrogels and allows self-healing and responsiveness to external stimuli which is essential for diverse applications by means of injection, pumping, or spraying, and thus renders the gels moldable. This approach is also superior to traditional methods because it does not require complex synthetic approaches or specialized small-molecule binding partners.

The present invention also provides methods for making such carriers, and for using such carriers in technical applications as an aqueous viscosity modifying delivery platform for fire retardants, fertilizers, pesticides, pipeline cleaning agents, and more. A use of such carriers as (biomimetic) scaffolds in tissue engineering, regenerative medicine, in drug and vaccine delivery, and pharmaceutical research is contemplated as well.

The above summary is not intended to include all features and aspects of the present invention nor does it imply that the invention must include all features and aspects discussed in this summary.

BRIEF DESCRIPTION OF THE DRAWINGS

The accompanying drawings illustrate embodiments of the invention and, together with the description, serve to explain the invention. These drawings are offered by way of illustration and not by way of limitation; it is emphasized that the various features of the drawings may not be to-scale.

(FIG. 3A) frequency-dependent oscillatory rheological properties of colloid silica-based trimeric hydrogels comprising HEC (0.85 wt %)/MC (0.15 wt %)/CSPs (5 wt %), (FIG. 3B) shear storage modulus and tan(delta) (G"/G') values (o)=10 rad/s, E=1%) values of colloid silica-based trimeric hydrogels comprising polymer (1 wt %)/CSPs (5 wt %) with various ratios of HEC (1300 kDa) and MC as well as (FIG. 3C) of colloid silica-based trimeric hydrogels comprising HEC (0.85 wt %)/MC (0.15 wt %)/CSPs (5 wt %) prepared with HEC of various molecular weights. (FIG. 3D) Strain-dependent oscillatory rheological properties of colloid silica-based trimeric hydrogels comprising HEC/MC (1 wt %)/CSPs (5 wt %) with varying HEC:MC ratios, (FIG. 3E) yield strain values taken from the oscillatory strain at deviation from the linear viscoelastic regime using colloid silica-based trimeric hydrogels comprising polymer (1 wt %)/CSPs (5 wt %) with various ratios of HEC (1300 kDa) and MC, and (FIG. 3F) yield strain values using colloid silica-based trimeric hydrogels comprising HEC (0.85 wt %)/MC (0.15 wt %)/CSPs (5 wt %) prepared with HEC of various molecular weights.

(FIG. 4A) steady-shear flow rheological properties of colloid silica-based trimeric hydrogels comprising HEC (0.85 wt %)/MC (0.15 wt %)/CSPs (5 wt %), (FIG. 4B) low-shear viscosity (0.1 s$^{-1}$) and shear-thinning index values for colloid silica-based trimeric hydrogels comprising polymer (1 wt %)/CSPs (5 wt %) with various ratios of HEC (1300 kDa) and MC, and (FIG. 4C) low-shear viscosity (0.1 s$^{-1}$) and shear-thinning index values for colloid silica-based trimeric hydrogels comprising HEC (0.85 wt %)/MC (0.15 wt %)/CSPs (5 wt %) prepared with HEC of various molecular weights. (FIG. 4D) Yield-stress measurements of colloid silica-based trimeric hydrogels comprising HEC/MC (1 wt %)/CSPs (5 wt %) with varying HEC:MC ratios. (FIG. 4E) Yield stress and yield viscosity values for colloid silica-based trimeric hydrogels comprising polymer (1 wt %)/CSPs (5 wt %) with various ratios of HEC (1300 kDa) and MC. (FIG. 4F) Yield stress and yield viscosity values for colloid silica-based trimeric hydrogels comprising HEC (0.85 wt %)/MC (0.15 wt %)/CSPs (5 wt %) prepared with HEC of various molecular weights.

(FIG. 8B) Steady-shear flow rheological properties of colloid silica-based trimeric hydrogel prepared in plain water or at high salinity (2% KCl). (FIG. 8C) Steady-shear flow rheological properties of colloid silica-based trimeric hydrogels prepared at different pH values ranging from pH 7.5 to pH 13. (FIG. 8D) Steady-shear flow rheological properties of colloid silica-based trimeric hydrogels prepared with colloidal silica nanoparticles of identical size, but with different surface compositions or stabilizing counter-ion: TM50 has an anionic silica surface and sodium counter-ion, AS40 has an anionic silica surface and an ammonium counter-ion, and TMA has a cationic aluminum surface and a chloride counter-ion.

(FIG. 9A) Steady-shear rheological properties of cellulose silica-based hydrogels comprising HEC (0.85 wt %)/MC (0.15 wt %)/CSPs (5 wt %) prepared at various pH values. (FIG. 9B) Yield-stress measurements of cellulose silica-based hydrogels comprising HEC (0.85 wt %)/MC (0.15 wt %)/CSPs (5 wt %) prepared at various pH values.

(FIG. 12A) Industrial wine production requires frequent pipeline cleaning and maintenance to limit contamination between products. Transfer of product through pipelines at the various stages of production typically leads to losses of approximately 2% of the total product volume. (FIG. 12B) Investigation of either KOH (1M; top) or cellulose silica-based hydrogel (bottom) for the removal of grape residue from aqueous solutions of Purple 8000 grape concentrate (10% v/v) allowed to foul a test pipe (d=½", l=24") for 1 h. (FIG. 12C) Aqueous solutions of Purple 8000 grape concentrate (10% v/v) were propelled through a test pipe (d=½", l=24") with one pipe volume (approximately 77 mL) of either water (top; consistent with industry standard practice) or cellulose silica-based hydrogel (bottom). (FIG. 12D) shows a graph of absorbance relative to volume for both gel and water. (FIG. 12E) By monitoring the absorbance of the Purple 8000 (λmax=535 nm) in the eluent over time, it was possible to determine the recovery of Purple 8000 from the pipeline (using a cut-off at dilution to 80%; error bars represent one standard deviation with n=3; P<0.0001 for both groups).

(FIG. 13A) Select cellulose silica-based hydrogels formulated with Phos-Chek LC95A fire retardant can be sprayed in a similar fashion as standard aqueous formulations of the retardant are applied, yet provide enhanced retention at the source of the fuel. (FIG. 13B) Thermal gravimetric analysis (TGA) of both treated and untreated model high-surface-area to volume fuel (e.g., pinewood flour) shows that the fire retardant both decreases the dramatic initial mass loss and inhibits subsequent mass loss. (FIG. 13C) Quantification of the mass remaining after the initial burn and the persistence of mass over time for untreated wood, wood treated with hydrogel alone, wood treated with aqueous retardant formulation, and wood treated with retardant-containing hydrogel formulation (error bars represent one standard deviation with n=3; P<0.0001 between samples treated with and without retardant). (FIG. 13D) TGA analysis of wood samples treated with standard aqueous retardant formulation and fire retardant-containing hydrogel formulation following simulated rainfall. Normalization was performed on the data, whereby 0% reflects the response of wood alone and 100% reflects the response of wood freshly treated with standard aqueous retardant formulation (error bars represent one standard deviation with n=3; P<0.0001 between samples with treated with gel and those treated with standard aqueous formulations).

DETAILED DESCRIPTION

Figure 1:
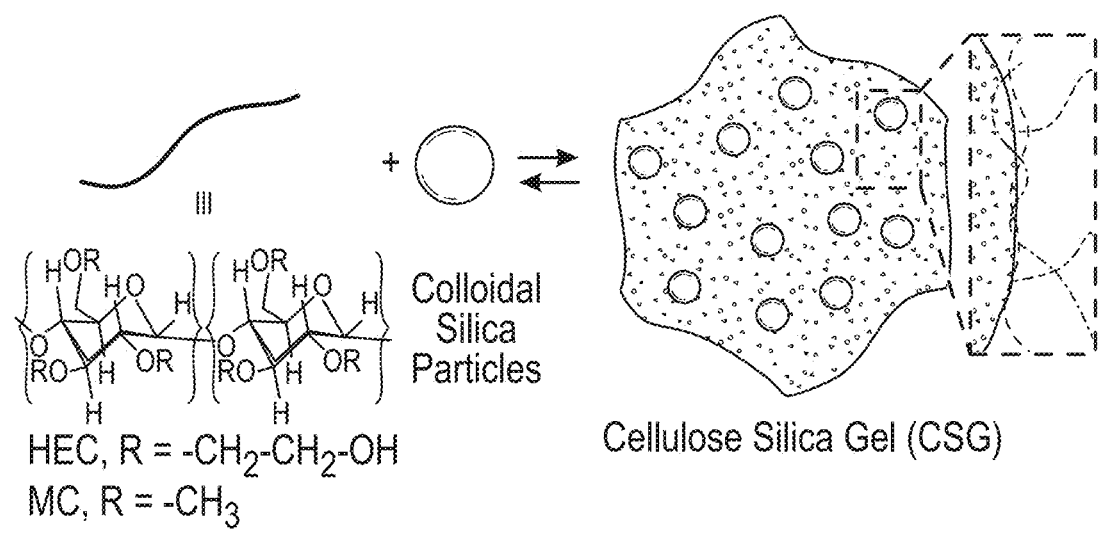
FIG. 1 illustrates that biomimetic moldable cellulose silica-based trimeric hydrogels are formed through self-assembly by exploiting multivalent and non-covalent interactions between colloidal silica nanoparticles and paired biopolymers such as cellulose derivatives including hydroxyethylcellulose (HEC) and methylcellulose (MC). Here, the biopolymer chains including HEC and MC are displayed in greyscale, while colloidal silica nanoparticles are displayed in orange. Trimeric hydrogel formation by self-assembly occurs upon mixing of all three component parts which allows for facile linear scaling of the formulation from 0.5 mL to over 15 L, but the hydrogel formation only occurs if the colloidal silica particles are mixed with pairs of biopolymers.
Figure 1:
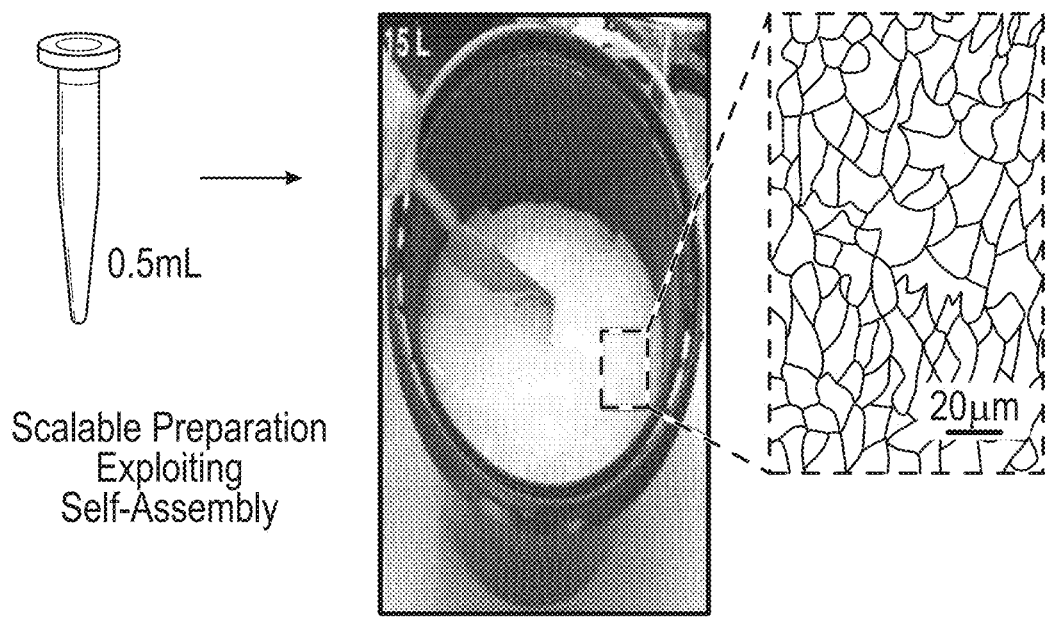

Compositions and methods are provided relating to scalable, biomimetic, moldable, self-assembled biopolymeric systems that find use as aqueous viscosity modifying carriers in various industrial and medical applications including as carriers of fire retardants, fertilizers, pesticides, and pipeline cleaning agents. Primary embodiments of the invention include scalable, biomimetic, moldable, self-assembled cellulose silica-based trimeric hydrogels formed through multivalent and non-covalent interactions with pairs of cellulose derivatives.

Scalable and moldable cellulose silica-based trimeric hydrogels can be prepared from environmentally safe, cost-effective and renewable polysaccharide starting materials and, therefore, present a unique solution to important industrial and environmental challenges that so far remained unsolved because of currently used materials' lack of scalability, lack of required mechanical properties, lack of environmental degradability, poor biocompatibility and unsustainable consumption of water.

In specific embodiments of the present invention, cellulose silica-based trimeric hydrogels find use in pipeline maintenance in the food and beverage manufacturing industry, as carriers of fire retardants, fertilizers, pesticides and more.

Before describing these specific embodiments of the invention, it will be helpful to set forth definitions that are used in describing the present invention.

1. Definitions

Unless defined otherwise, all technical and scientific terms used herein have the same meaning as commonly understood by a person of ordinary skill in the art to which this invention belongs. The following definitions are intended to also include their various grammatical forms, where applicable. As used herein, the singular forms "a" and "the" include plural referents, unless the context clearly dictates otherwise.

The term "colloidal silica," as used herein, refers to silicon dioxide and, in particular, to synthetic silica including pyrogenic silica and precipitated silica, in crystalline as well as non-crystalline (amorphous) form. Colloidal silica includes colloidal silica particles and colloidal silica nanoparticles.

The term "hydrogel," as used herein, refers to an aqueous polymeric system that is formed by multivalent and non-covalent interactions and crosslinking of polymerizing components, and is void of covalent interactions and crosslinks.

The terms "trimer" and "trimeric," as used herein, relate to the formation of a polymeric system, in particular a hydrogel, from a three-components set-up. Thus, a trimeric hydrogel represents a three-component hydrogel. In a cellulose silica-based trimeric hydrogel, one component is colloidal silica and the other two components are pairs of cellulose derivatives that only form a hydrogel with colloidal silica when both components of the cellulose derivatives pair are present, but that do not form a hydrogel with colloidal silica if only one of the cellulose derivatives pair is present.

The term "shear-thinning," as used herein, relates to the process of a hydrogel thinning under the application of tension to the point where the hydrogel starts to flow.

The term "self-healing," as used herein, relates to the process of a flowing hydrogel to reforming to a non-flowing hydrogel once the applied tension is relaxed or removed.

The term "moldable hydrogel," as used herein, relates to a hydrogel that thins upon the application of tension and rapidly self-heals once the tension is relaxed or removed.

The term "biodegradable," as used herein, relates to materials that decompose under natural conditions and are capable of being decomposed by living organisms.

The term "colloidal silica," as used herein, relates to a stable dispersion of silica particles, typically ranging from about 1 to 100 nm.

The term "viscosity modifier" or "viscosity modification," as used herein, relates to a change of flowability that is obtained by the addition of a hydrogel, as described herein.

The term "biomimetic scaffold," as used herein, relates to a three-dimensional matrix that is derived from natural body tissues or synthetic materials and that supports metabolic activities, provides biomechanical strength for tissue reconstruction in humans as well as animals, and permits typical cell type interactions in tissues. Such scaffolds can include agents such as growth factors, e.g. TGF-beta, VEGF, PDGF, BMPs, NGFs, small molecule drugs, proteins, peptides, and other additives, to enhance stability of the scaffold and to aid tissue regeneration.

The term "cosmetic agent," as used herein, relates to molecules and articles that are applied to the human face or body for skin cleansing or beautifying.

The term "small molecule," as used herein, relates to molecules with a molecular weight of less than 1000 daltons and having biological or pharmacological activity.

The term "pharmacologically active/activity" or "biologically active/activity," as used herein, relate to an effect that is useful in the treatment or diagnosis of a disease or disorder or that affects the function of the body of a human or an animal.

2. Polymeric Systems

In one aspect, the present invention is directed to compositions relating to scalable, biomimetic, moldable, self-assembled biopolymeric systems that find use as cost-effective, renewable and biodegradable aqueous viscosity modifying carriers. Primary embodiments of the invention include scalable, biomimetic, moldable, self-assembled cellulose silica-based trimeric hydrogels formed by combining colloidal silica nanoparticles with pairs of polysaccharides which are produced from renewable, environmentally safe and cost-effective starting materials and which are suitable to a range of industrial applications. These compositions promise broad utility as inert and safe carriers for a variety of cargo. In exemplary embodiments, the applicability of these compositions is demonstrated as carriers for pipeline maintenance in the food and beverage industries, and as carriers of fire retardants for effective and affordable wildland fire management.

Moldable cellulose silica-based hydrogels are formed and maintained through specific and tunable multivalent and non-covalent interactions and crosslinking as evidenced by their ability to exhibit viscous flow under shear stress (shear-thinning) and rapid recovery when the applied stress is relaxed (self-healing). In contrast to traditional chemically cross-linked materials, such multivalent and non-covalent interactions and crosslinking allow for precise tuning of flow properties to meet the engineering requirements for diverse applications, including injection, pumping, or spraying.

Select cellulose derivatives have been reported to adsorb onto colloidal silica particles (Kapsabelis and Prestidge, 2000). The complementary affinity between polymers and silicates emulates natural systems and has been utilized to fabricate biomimetic hydrogels of incredible strength (Wang et al., 2010; Tamesue et al., 2013).

Polysaccharides Suitable for Forming Trimeric Hydrogels with Colloidal Silica Nanoparticles Polysaccharides suitable for forming trimeric hydrogels with colloidal silica nanoparticles must be capable of selectively adsorb to colloidal silica particles via multilateral and non-covalent interactions.

Naturally occurring polysaccharides are polymers of carbohydrates such as starch, glycogen, alginate, agarose, cellulose whose properties depend on their chemical structure, functional groups, linkage, conformation, and more. Ring-opening polymerization, enzyme-catalyzed polymerization and other methods of polymerization have made possible the production of synthetic polysaccharides. Both naturally occurring and synthetic polysaccharides are contemplated as being suitable for use in the present invention, particularly derivatives of cellulose.

Chemically modified derivatives of cellulose are widely used in the industrial sector and can be obtained, for example, by esterification (acetylation, sulphation), carbanilation, and etherification of cellulose. Exemplary cellulose derivatives include cellulose acetate, cellulose nitrate, cellulose xanthate, carboxymethylcellulose, methylcellulose, ethylcellulose, hydroxyethylcellulose.

Commercially available polysaccharide compounds, including cellulose derivatives, were screened in a concentration of 1% mass/volume (1 wt. %) for their ability to form hydrogels with colloidal silica particles ($D_H$~15 nm) in concentrations of 1-10 wt. % under ambient conditions.

Among the cellulose derivatives, hydroxyethylcellulose (HEC) and methylcellulose (MC) were identified to rapidly form robust trimeric hydrogels when mixed with colloidal silica particles. In each case, hydrogel formation required the presence of colloidal silica particles and both (paired) cellulose derivatives, as solutions of colloidal silica particles (1-10 wt %) and cellulose derivatives (1 wt %) alone were each low viscosity liquids.

In various embodiments of the invention, pairs of cellulose derivatives were utilized to form cellulose silica-based trimeric hydrogels, whereby various combinations of the pair hydroxyethylcellulose (HEC) and methylcellulose (MC) gave the best results.

Colloidal Silica Particles Suitable for Hydrogel Formation with Pairs of Cellulose Derivatives by Way of Multivalent and Non-Covalent Interactions and Crosslinking In various embodiments of the invention, colloidal silica nanoparticles form moldable hydrogels by selective, pH-dependent adsorption to paired cellulose derivatives via multivalent and non-covalent interactions and crosslinking. This approach affords unique control over the flow properties of the cellulose silica-based hydrogels and allows self-healing and responsiveness to external stimuli which is essential for diverse applications by means of injection, pumping, or spraying; this approach is also superior to traditional methods because it does not require complex synthetic approaches or specialized small-molecule binding partners.

Colloidal silica nanoparticles suitable for forming trimeric hydrogels with pairs of cellulose derivatives require a particular surface chemistry meaning that they have a silica surface that substantially (at least 80%) or exclusively consists of silanol (SiOH) groups and is negatively charged in a pH dependent manner.

3. Methods of Use

In another aspect, the invention provides methods for making such compositions, and for using them as carriers in in various industrial, technical and medical applications as an aqueous viscosity modifying delivery platform for fire retardants, fertilizers, pesticides, pipeline cleaning agents, and more. A use of such carriers as biomimetic scaffolds in tissue engineering, regenerative medicine, in drug and vaccine delivery, and pharmaceutical research is contemplated as well.

Fire Retardants

Fire retardant agents or fire retardants are substances that slow or stop the spread of fire. Phos-Check fire retardants, some of which were used in the experiments described herein, are mixed with water and applied to homes, trees and vegetation when there is a risk of a wild fire in the area. Fire retardants usually include phosphates such as mono-ammonium or diammonium phospate, ammonium polyphosphate, or sulfates such as diammonium sulfate.

Chemical Treatment with Fertilizers

Fertilizers support and enhance the growth of plants and are commonly used in liquid or solid form for growing crops. A typical fertilizer contains nitrogen, phosphorus, or potassium. Many of the above mentioned fire retardant phosphates and sulfates double as fertilizers. Since excess fertilization is counterproductive, fertilizer must be applied carefully and efficiently.

Chemical Treatment with Pesticides

Pesticides are chemical or biological agents that regulate the growth of weeds (herbicides) and pests (pesticides). Since pesticides can have toxic effects in humans and animals when ingested accidentally, pesticides must be applied in a controlled fashion.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible. In the following, experimental procedures and examples will be described to illustrate parts of the invention.

EXPERIMENTAL PROCEDURES

The following methods and materials were used in the examples that are described further below.

Cellulose Silica-Based Trimer Hydrogel Preparations

Cellulose silica-based trimer hydrogels were prepared by first dissolving hydroxyethyl-cellulose (HEC; $M_v$~1300 or 720 kDa; Sigma) and/or methylcellulose (MC; $M_v$~90 or 60 kDa; Sigma) in water (30 mg/mL) with stirring and mild heating. Colloidal silica particles (CSPs; Ludox TM-50; $D_H$~15 nm; 50% w/w; Sigma) were diluted to 15 wt % solutions. HEC/MC polymer solution (150 µL) and CSP solution (300 µL) were then added together and mixed well by vortex (some samples were mildly centrifuged to remove bubbles arising from mixing). Large-volume preparation of cellulose silica-based trimer hydrogels used the same ratios scaled linearly, and mixing was performed with an impeller mixer.

Cellulose Silica-Based Hydrogel Characterization

Rheological characterization was performed using a TA Instruments AR-G2 controlled-stress rheometer fitted with a Peltier stage. All measurements were performed using a 25 mm plate geometry and analyzed using TA Instruments TA Orchestrator software. SEM images where acquired using a FEI XL30 Sirion microscope using a beam voltage of 5 kV. Lyophilized samples were pressed onto carbon paint and sputter coated with Au/Pd (60:40) prior to imaging.

Pipeline Pigging Experiments

Two experiments were designed to investigate the performance of the cellulose silica-based trimer hydrogels in pigging applications. For the first experiment, to simulate wine product movement, an aqueous solution of Purple 8000 grape concentrate (10% v/v) was pumped into a test pipe (d=½", l=24"), followed immediately by either hydrogel (prepared as mentioned above) or water (control experiment consistent with industry practice). The absorbance ($ä_{max}$=535 nm) of the eluent was monitored over time at varying flow rates. Analysis of the proportion of aqueous Purple 8000 recovered from the pipe was determined utilizing a cut-off at 80% dilution. For the second experiment, to simulate pipeline cleaning, Purple 8000 solutions were pumped into the test pipe and allowed to settle for 1 h before draining. Following this, either hydrogel (prepared as mentioned above) or water was pumped through the pipe at varying flow rates for cleaning. Analysis of cleaning potential was determined by monitoring absorbance ($ä_{max}$=535 nm) of the eluent over time. All experiments were performed in triplicate.

Fire Prevention Experiments

Two experiments were designed to investigate the performance of the cellulose silica-based trimer hydrogels as carriers of fire retardants in fire prevention applications. Initially, wood flour (System Three, Inc.) was dried at 120° C. under vacuum for 24 h. Dry wood flour (100 mg) was mixed with each treatment (20 mg), including water (control), gel, fire retardant solution, and gel containing fire retardant. Each treatment group was dried at 120° C. under vacuum for 24 h prior to analysis. Utilizing thermal gravimetric analysis (TGA), samples (~20 mg) were heated at a rate of 50° C./min to 500° C., and then maintained at 500° C. for 15 min while monitoring weight loss. Subsequently, each treatment group was subjected to simulated rain, whereby samples were washed with water with vigorous shaking (1 mL for 10 s), isolated by filtration, and dried at 120° C. under vacuum for 24h prior to TGA analysis. All experiments were performed in triplicate.

EXAMPLES

The following examples are put forth so as to provide those of ordinary skill in the art with a complete disclosure and description of how to make and use the present invention; they are not intended to limit the scope of what the inventors regard as their invention. Unless indicated otherwise, part are parts by weight, molecular weight is average molecular weight, temperature is in degrees Centigrade, and pressure is at or near atmospheric.

Example 1

Biomimetic Cellulose Silica-Based Hydrogel Formation [and Characterization]

Within the field of self-assembly, interactions between polymers and nano-sized particles have arisen as a simple route to assemble tunable and self-healing polymeric materials without the need for complex synthetic approaches or specialized small-molecule binding partners (Rose et al., 2014; Appel et al., 2015a; Appel et al., 2015b). The complementary affinity between polymers (molecular binders) and hard nanoparticles (clay nanosheets/silicates) emulates natural systems and has been utilized to fabricate biomimetic hydrogels of incredible strength (Wang et al., 2010; Tamesue et al., 2013).

Herein, we report the preparation and application of biomimetic cellulose silica-based hydrogels driven by non-covalent interactions between renewable and environmentally benign polysaccharides and colloidal silica particles, as shown in FIG. 1. Polysaccharides provide an attractive starting material on account of their availability from renewable resources, aqueous solubility, high molecular weight, diverse chemical functionality, low cost, environmental-degradability, biocompatibility, and large scale production (Rose et al., 2014). Moreover, colloidal silica particles are produced on large scale and utilized across many fields and technologies ranging from personal care products to fining agents in industrial beer and wine production, and yet many fundamental questions regarding the formation and behavior of colloidal silica composites and systems are still not fully addressed (Bergna and Roberts, 2005).

Conditions for Hydrogel Formation From Polymer and Colloidal Silica Nanoparticles Efficient cross-linking in polymer-nanoparticle hydrogels necessitates three criteria: (i) a strong affinity between the nanoparticles and the polymer chains, i.e., the free energy gain (E) resulting from adsorption of a polymer chain to the surface of a nanoparticle should be greater than or comparable to the thermal energy ($k_B T$); (ii) the nanoparticle diameter should be comparable to, or less than, the persistence length ($l_p$) of the polymer strands (required to favor polymer bridging of multiple nanoparticles over polymer wrapping around individual particles); and (iii) the number density of polymers and particles must allow for an average at least two interactions per particle and polymer to comprise a cross-linked network (Appel et al., 2015a). When these criteria are met, hydrogel formation is favored over the alternative conformations.

Materials

Commercially available polysaccharide compounds in a concentration of 1% mass/volume (1 wt. %) were screened for their ability to form hydrogels with colloidal silica particles ($D_H$~15 nm) in concentrations of 1-10 wt. % under ambient conditions. Through qualitative screens hydroxyethylcellulose (HEC) and methylcellulose (MC) were identified to rapidly form robust hydrogels when mixed with colloidal silica particles, as shown Table 1 with a '+' in the performance column (far right). In each case, hydrogel formation required the presence of both colloidal silica particles and cellulose derivatives, as solutions of colloidal silica particles (1-10 wt %) and cellulose derivatives (1 wt %) alone are each low viscosity liquids.

TABLE 1

Screening of commercial polysaccharides for their ability to form hydrogels with colloidal silica (SiNP).

| Entry | Polymer[a] | [Polymer] (%) | NP | [NP] (%) | Performance[b] |
|---|---|---|---|---|---|
| 1 | HPMC | 1 | SiNP | 1 | -- |
| 2 | HPMC | 1 | SiNP | 5 | -- |
| 3 | HPMC | 1 | SiNP | 10 | -- |
| 4 | Guar Gum | 1 | SiNP | 1 | -- |
| 5 | Guar Gum | 1 | SiNP | 5 | - |
| 6 | Guar Gum | 1 | SiNP | 10 | + |
| 7 | Xanthan Gum | 1 | SiNP | 1 | -- |
| 8 | Xanthan Gum | 1 | SiNP | 5 | -- |
| 9 | Xanthan Gum | 1 | SiNP | 10 | -- |
| 10 | Karaya Gum | 1 | SiNP | 1 | -- |
| 11 | Karaya Gum | 1 | SiNP | 5 | -- |
| 12 | Karaya Gum | 1 | SiNP | 10 | -- |
| 13 | Locust Bean Gum | 1 | SiNP | 1 | -- |
| 14 | Locust Bean Gum | 1 | SiNP | 5 | -- |
| 15 | Locust Bean Gum | 1 | SiNP | 10 | -- |
| 16 | Hyaluronic Acid | 1 | SiNP | 1 | -- |
| 17 | Hyaluronic Acid | 1 | SiNP | 5 | -- |
| 18 | Hyaluronic Acid | 1 | SiNP | 10 | -- |
| 19 | CMC | 1 | SiNP | 1 | -- |
| 20 | CMC | 1 | SiNP | 5 | -- |
| 21 | CMC | 1 | SiNP | 10 | - |
| 22 | HEC | 1 | SiNP | 1 | + |
| 23 | HEC | 1 | SiNP | 5 | + |
| 24 | HEC | 1 | SiNP | 10 | ++ |
| 25 | MC | 1 | SiNP | 1 | + |
| 26 | MC | 1 | SiNP | 5 | ++ |
| 27 | MC | 1 | SiNP | 10 | ++ |

[a]HPMC = hydroxypropylmethylcellulose, CMC = carboxymethylcellulose, HEC = hydroxyethyl-cellulose, and MC = methylcellulose.
[b]Qualitative measure of performance based on a finger flick assay assessing overall material properties and propensity for rapid self-healing following shear-thinning. In these tests, an inverted vial of the prepared materials is physically disturbed by a finger flick. The resulting shear-dependent flow and subsequent self-healing was observed and rated.

Subsequently a series of trimeric hydrogels with various combinations of HEC, MC and colloidal silica, as listed in Table 2, was prepared to optimize the formulation for initial mechanical properties, self-healing behavior and stability over time. In these experiments the total concentration of polysaccharides was maintained at 1 wt % while the colloidal silica particle concentration ranged from 1-5 wt %.

Figure 2A:
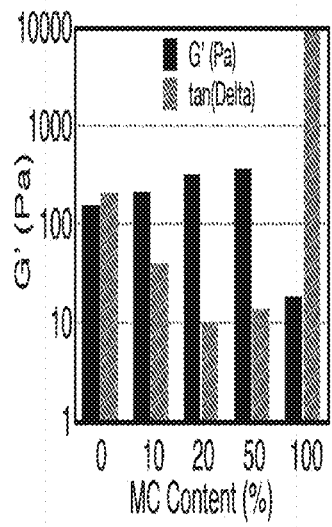
FIGS. 2A-2F provides an overview over oscillatory rheological properties of various cellulose silica-based hydrogels that were prepared from (FIG. 2A) polymer (1 wt %) and colloidal silica (5 wt %) at various loadings (percentages) of methylcellulose (MC) in the polymer fraction ranging from 0-100% MC content, (FIG. 2B) hydroxyethlycellulose/methylcellulose combinations (HEC/MC) (80:20 w/w %) and colloidal silica at various ratios, and (FIG. 2C) HEC (1.2 wt %)/MC (0.3 wt %)/colloidal silica (7.5 wt %). All values were collected at $\omega=10$ rad/s, $\epsilon=2\%$, 25° C. Using a cellulose silica-based trimeric hydrogel prepared from HEC (1.2 wt %)/MC (0.3 wt %)/colloidal silica (7.5 wt %) in FIG. 2D-2F, (FIG. 2D) strain-dependent ($\omega=10$ rad/s, 25° C.) and (FIG. 2E) frequency-dependent ($\epsilon=2\%$, 25° C.) oscillatory shear rheological properties were determined, and (FIG. 2F) steady shear rheological properties.

While all tested formulations demonstrated good-to-excellent mechanical properties and self-healing tendencies initially, as shown in FIG. 2A, many of them suffered from syneresis over time, as shown in Table 2. Yet, at HEC:MC ratios of 80:20, strong, yet elastic hydrogels were formed with colloidal silica particles, and mechanical properties were maintained for at least one week, as indicated by a shear storage modulus of G'~500 Pa ($\omega$)=10 rad/s, $\gamma$=2%) as a measure of hydrogel strength, and a high storage-to-loss oscillatory shear modulus ratio as a measure of hydrogel elasticity (with a loss oscillatory shear modulus G"; tan $\delta$(tan $\delta$=G"/G').

TABLE 2

Screening of HEC/MC-based colloidal silica (SiNP) - based hydrogels for their long-term stability.

| Entry | [HEC] (%) | [MC] (%) | [SiNP] (%) | Initial Performance[a] | Stability[b] |
|---|---|---|---|---|---|
| 1 | 0.5 | 1 | 1 | + | - |
| 2 | 0.5 | 1 | 5 | ++ | - |
| 3 | 0.6 | 0 | 1 | + | - |
| 4 | 0.6 | 0 | 5 | ++ | - |
| 5 | 0.7 | 0 | 1 | + | + |
| 6 | 0.7 | 0 | 5 | ++ | ++ |
| 7 | 0.8 | 0 | 1 | ++ | ++ |
| 8 | 0.8 | 0 | 5 | ++ | ++ |
| 9 | 0.9 | 0 | 1 | + | - |
| 10 | 0.9 | 0 | 5 | + | - |

[a]Qualitative measure of performance based on overall material properties and propensity for rapid self-healing following shear-thinning.
[b]Qualitative measure of hydrogel stability after 1 week storage at room temperature assessing retention of functional performance and stability against syneresis.

Interestingly, if colloidal silica particles of a different surface chemistry were used (Ludox TMA), the resulting hydrogels exhibited dramatically different mechanical properties, as shown in FIG. 3. TMA-based materials, despite having only a slightly reduced G' value, exhibited a much higher tan $\delta$ value, and consequently, a much higher degree of fluidity. These data indicated that selective adsorption of the modified cellulose chains (in HEC and MC) to colloidal silica particles (CSP) enabled cross-linking and gel formation, supporting a physical picture of gel assembly.

Contribution of Polymer Molecular Weight

Using a formulation of HEC (0.8%):MC (0.2%):CSP (5%), the contribution of polymer molecular weight to the overall mechanical performance, including long-term stability, was investigated with cellulose silica-based hydrogels comprising combinations of high and low molecular weight HEC and MC polymers, as shown in Table 3.

TABLE 3

Screening of HEC/MC/CSP hydrogels for the dependence of long-term stability on molecular weight of the polymers[a].

| Entry | HEC[b] | MC[c] | Initial Performance[d] | Stability[e] |
|---|---|---|---|---|
| 1 | high | high | ++ | + |
| 2 | high | low | ++ | ++ |
| 3 | low | high | + | + |
| 4 | low | low | − | − |

[a]All formulations contained HEC (0.8%): MC (0.2%): CSPs (5%)
[b]HEC: high = 1.3 MDa, low MW = 720 kDa.
[c]MC: high MW = 90 kDa, low MW = 60 kDa.
[d]Qualitative measure of performance based on overall material properties and propensity for rapid self-healing following shear-thinning.
[e]Qualitative measure of hydrogel stability after 1 week storage at room temperature assessing retention of functional performance and stability against syneresis.

From these studies, it became apparent that HEC molecular weight was the primary determinant of hydrogel strength, whereby a decrease in molecular weight from $M_v$~1300 to $M_v$~720 kDa resulted in a dramatic decrease in material properties. In contrast, lowering the MC molecular weight from $M_v$~90 to $M_v$~60 kDa exhibited no significant decrease in the initial material properties, yet improved gel stability over time. While only two different molecular weights were examined for each polymeric component, these results indicate that polymer molecular weight can be exploited to tune gel properties.

Figure 2B:
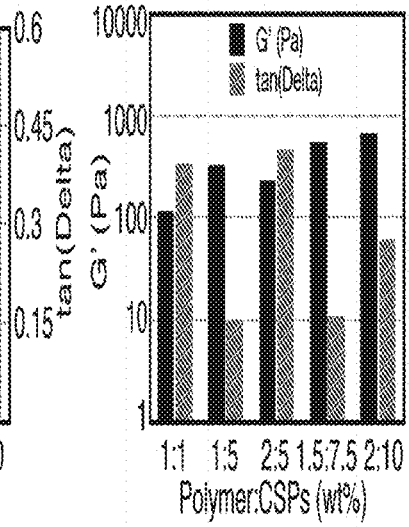

Following the initial component screen, the impact of component loading and stoichiometric polymer-to-colloidal-silica particle ratio on the resulting hydrogel behavior was determined, as shown in FIG. 2B. A stoichiometric polymer-to-colloidal-silica particle ratio of 1:5 maximized hydrogel strength and elasticity as indicated by a high value of shear storage modulus (G') and a low storage-to-loss oscillatory shear modulus ratio (tan δ), while deviation from the stoichiometric polymer-to-colloidal-silica particle ratio (either with more polymer or more CSPs) led to lower G' values and more fluid-like materials. Interestingly, increasing the overall loading of these components while maintaining the stoichiometric polymer-to-colloidal-silica particle ratio of 1:5 increased G' while leaving tan δ unchanged, indicating a maintenance of the overall degree of elasticity.

Figure 2C:
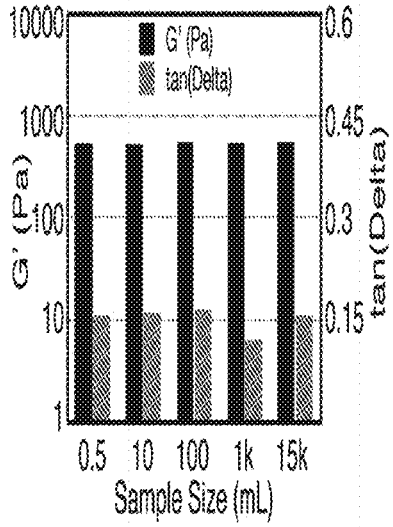

Based on these formulation results, the reproducibility and scalability of trimeric HEC:MC: colloidal silica particle (CSP) hydrogels were investigated. Hydrogels comprising HEC (1.2 wt %):MC (0.3 wt %):CSP (7.5 wt %) were prepared four times in parallel and the mechanical properties demonstrated excellent reproducibility, as shown in FIG. 4. Subsequently their production was scalable in a linear fashion from 0.5 mL to over 15 L, as shown in FIG. 2C, demonstrating the self-assembly approach as an extremely powerful and industrially scalable tool for trimeric HEC: MC:CSP hydrogels formation, as the manufacturing of these hydrogels can easily be scaled in a linear fashion over 4.5 orders of magnitude without resulting in an alteration of their mechanical properties.

Trimeric HEC:MC:CSP hydrogels are easily scalable because the gel formation and mechanical properties are solely dependent on the selective adsorption between cellulose derivatives and colloidal silica particles, which, on the molecular size-scale, is indifferent to total production volume.

Figure 2D:
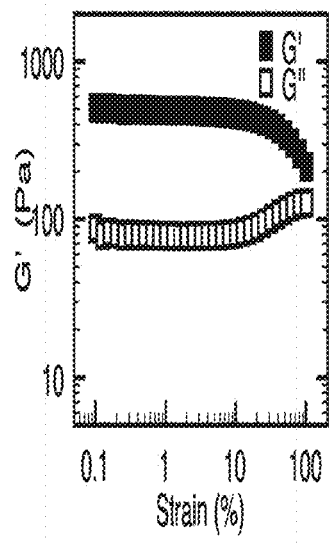
Figure 2E:
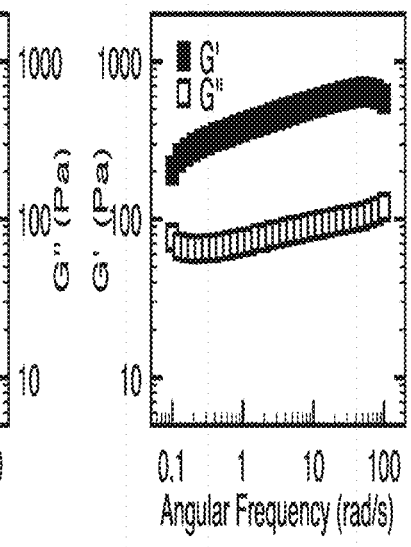
Figure 2F:
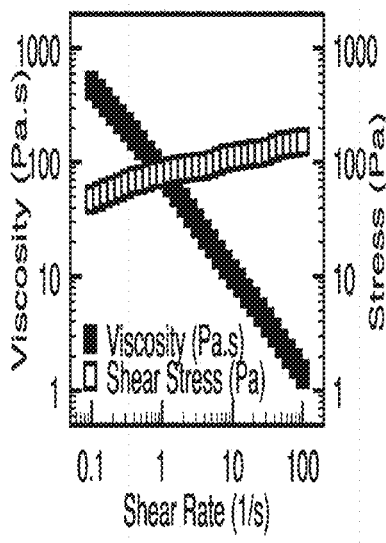

As shown in FIG. 2D, strain-dependent oscillatory rheology of trimeric HEC (1.2 wt %):MC (0.3 wt %):CSP (7.5 wt %) hydrogels displayed an extremely broad linear viscoelastic regime, and network failure occurring only at high strains (>20%), indicating a wide processing range and shear-thinning behavior. The frequency dependence of the storage and loss oscillatory shear moduli in the linear viscoelastic regime confirmed hydrogel-like behavior, as G' was dominant across the whole range of frequencies observed (0.1-100 rad/s, as shown in FIG. 2E). Moreover, the observed shear-thinning behavior was corroborated with steady shear rheometrical measurements, as shown in FIG. 2F, which indicated that the materials exhibit a power law decrease in viscosity with increasing shear rate.

Library of Cellulose Silica-Based Trimer Hydrogels with Different Pairs of Hydroxyethylcellulos and Methylcellulose A library of cellulose silica-based trimer hydrogels was created with various combinations of HEC and MC as well as with HEC of various molecular weight to engineer a range of materials with highly disparate mechanical properties and tunable responsiveness to environmental conditions.

Figure 3A:
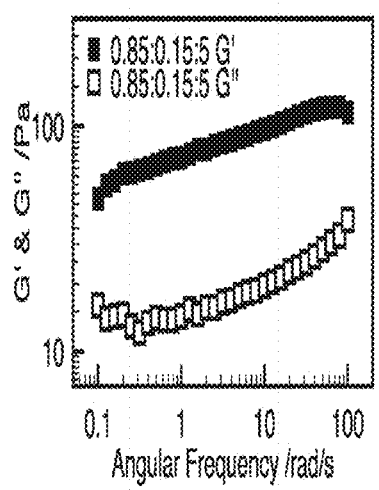
FIGS. 3A-3F provides a further overview over oscillatory rheological properties obtained from various colloid silica-based trimeric hydrogels.
Figure 3B:
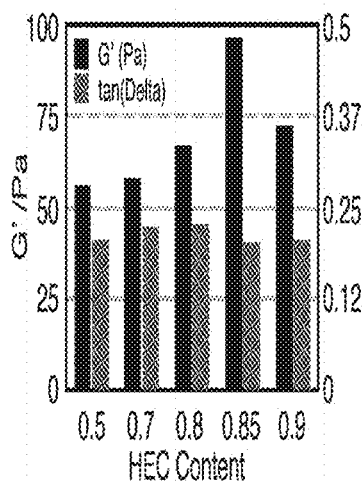
Figure 3C:
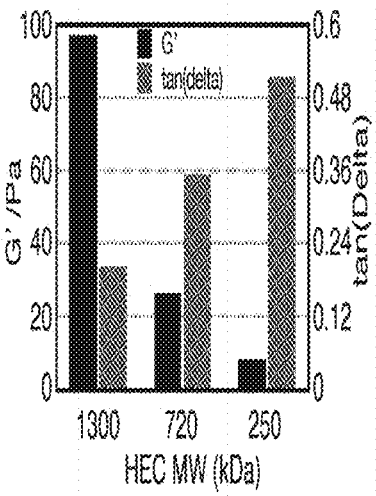
Figure 3D:
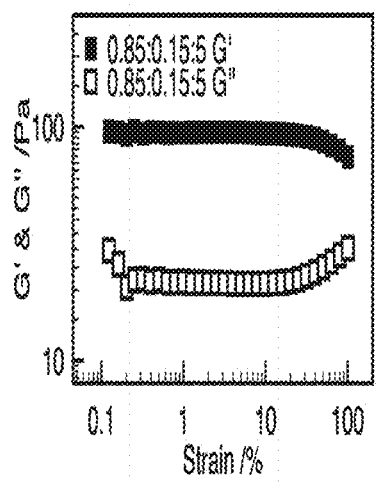
Figure 3E:
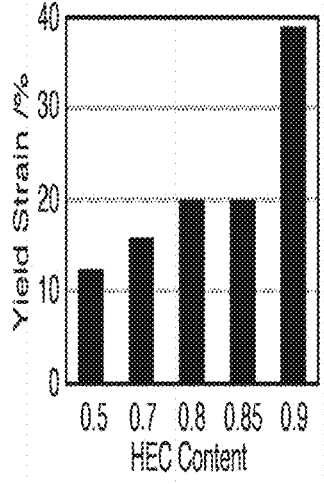
Figure 3F:
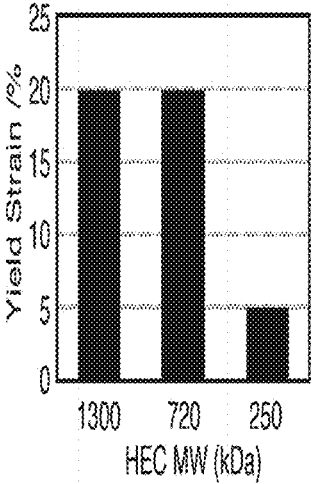
Figure 4A:
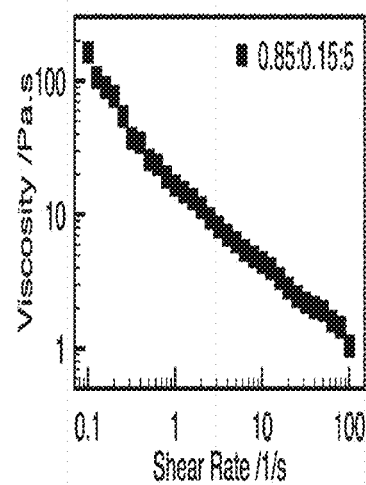
FIGS. 4A-4F illustrates flow rheological properties of colloid silica-based trimeric hydrogels.
Figure 4B:
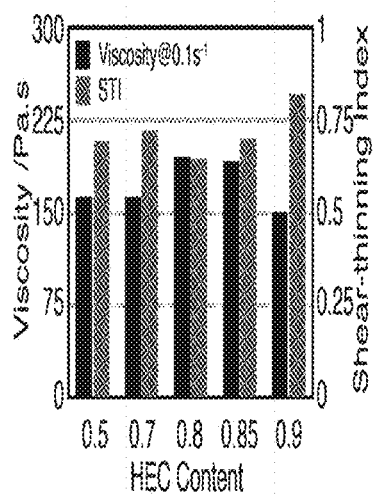
Figure 4C:
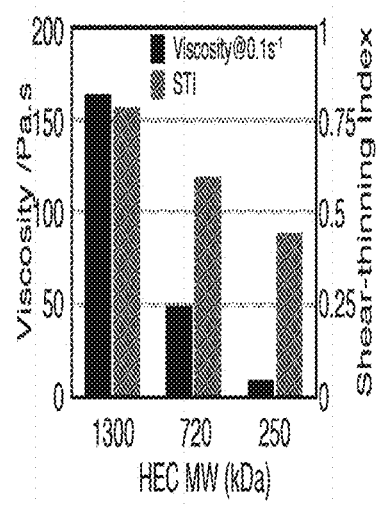
Figure 4D:
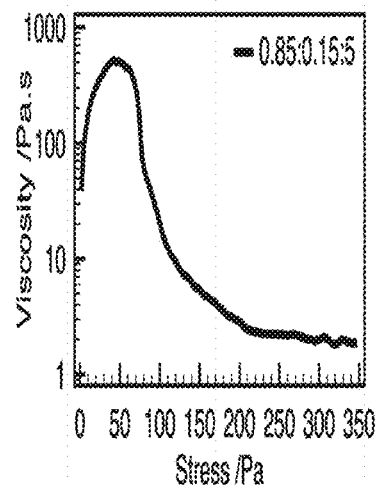
Figure 4E:
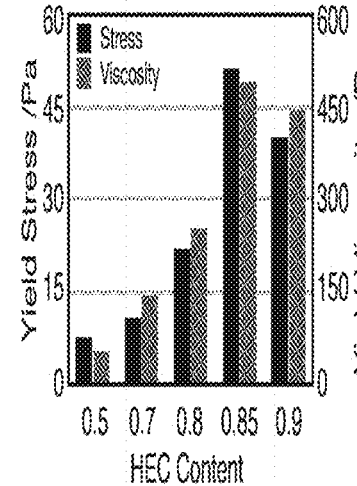
Figure 4F:
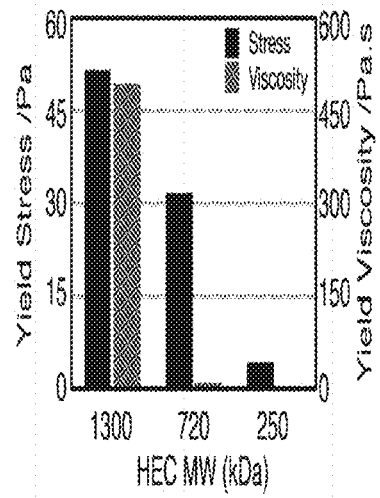

In these experiments the total concentration of polymer was maintained at 1 wt %, CSP concentration was kept at 5 wt %, and the ratio of HEC to MC was altered. According to frequency-dependent oscillatory rheological measurements performed in the linear viscoelastic regime, the shear storage modulus (G') was much greater than the loss modulus (G") throughout the entire observed frequency range, indicating hydrogel formation. As explained above, G' is reported as a measure of hydrogel strength, and tanδ (tan $\delta$=G"/G') as a measure of hydrogel elasticity. As shown in FIGS. 3A-3C, alteration of the formulation allows for tuning of G' from 10 to roughly 100 Pa with ω=10 rad/s and γ=2% simply by changing the ratio of HEC to MC while keeping the overall ratio of polymer to CSP ratio constant (polymer 1%: CSP 5%), or by changing the molecular weight of the HEC while keeping the formulation constant. The results in FIG. 3B, furthermore, indicate that, while G' is modulated through alteration of the ratio of HEC to MC, the tanδ remains unchanged.

Figure 5:
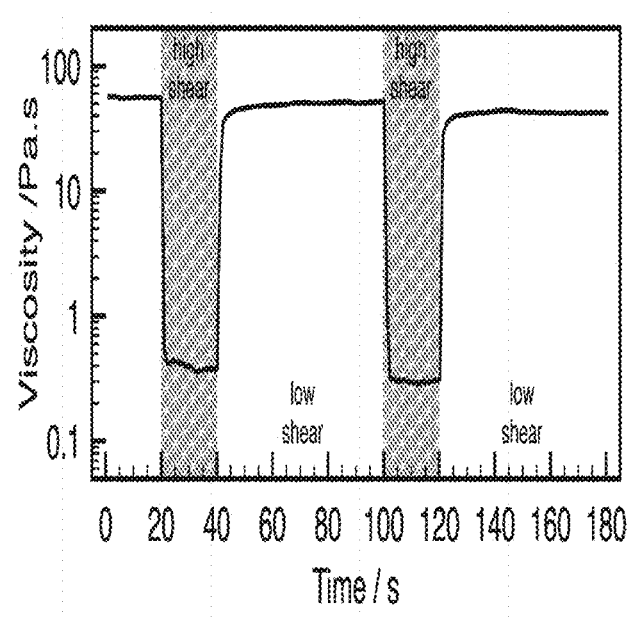
FIG. 5 shows step-shear measurements of colloid silica-based trimeric hydrogels comprising HEC (0.85 wt %)/MC (0.15 wt %)/CSPs (5 wt %) over two cycles of high shear (100 s$^{-1}$) and low shear (0.1 s$^{-1}$) demonstrating rapid (less than 5 s) and complete recovery of mechanical properties.

Strain dependent oscillatory rheology (FIG. 3D-3E) of these materials displayed an extremely broad linear viscoelastic regime and network failure only at high strains (>10%), indicating a wide processing range and shear-thinning behavior. Moreover, the observed shear-thinning behavior was corroborated with steady shear rheometrical measurements (FIG. 4a-c), which indicated that the materials exhibit a power-law decrease in viscosity with increasing shear rate. The shear-thinning index reported in FIG. 4 refers to the power law exponent from fitting of the viscosity versus shear rate obtained in a steady-shear measurement. Meanwhile the materials also exhibit rapid self-healing properties from the step-shear measurement (FIG. 5) where the cellulose silica-based hydrogels go through two cycles of breaking and healing. Under a high shear rate, the materials break and show low viscosity, but under a subsequent low shear rate the materials completely restore to the original viscosity in less than 5 seconds, demonstrating rapid self-healing. When the hydrogel is sheared at a high rate, chains are placed under tension and desorb from the particles to relax stress, allowing the gel to flow. Upon relaxation of the applied shear, the hydrogels can rapidly re-form as polymers re-adsorb to particles in a new configuration.

Figure 6A:
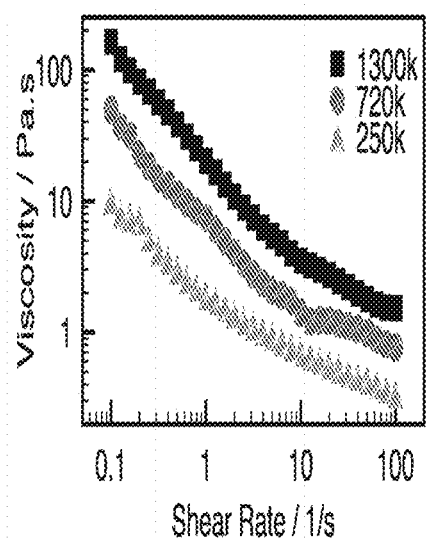
FIG. 6A illustrates steady-shear rheological properties and FIG. 6B illustrates yield-stress measurements of colloid silica-based trimeric hydrogels comprising HEC (0.85 wt %)/MC (0.15 wt %)/CSPs (5 wt %), demonstrating the mechanical impact of altering the HEC molecular weight from 1300 to 720 and to 250 kDa.
Figure 6B:
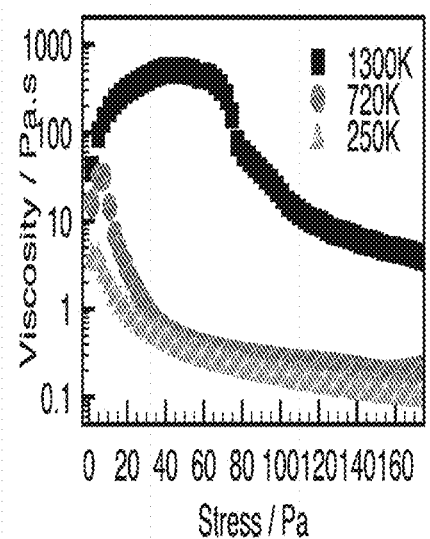

Flow rheology was also characterized with yield-stress measurements. These materials exhibit shear-thinning behavior (FIGS. 4D-4F; FIG. 6). Importantly, both the magnitude of the viscosity and the degree of shear-thinning can be broadly tuned through alteration of the formulation.

Figure 7:
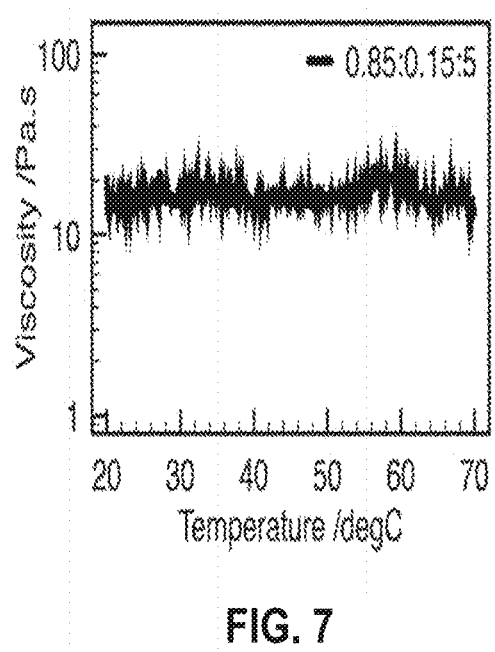
FIG. 7 shows a temperature ramp of a colloid silica-based trimeric hydrogel comprising HEC (0.85 wt %)/MC (0.15 wt %)/CSPs (5 wt %) in flow ($\gamma=0.5$ s$^{-1}$), demonstrating that the hydrogel's mechanical response is not affected by temperature, at least in the range of 20 to 70 degree Celsius.
Figure 8A:
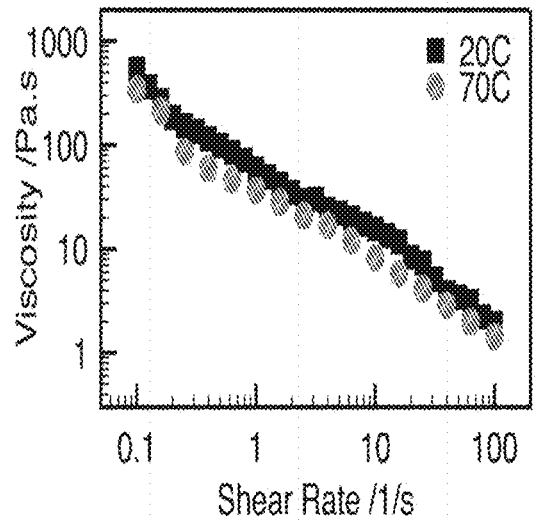
FIGS. 8A-8D illustrates the stimuli-responsiveness of colloid silica-based trimeric hydrogels comprising HEC (0.85 wt %)/MC (0.15 wt %)/CSPs (5 wt %): (a)(FIG. 8A) Steady-shear flow rheological properties at 20 and 70 degree Celsius.

The responsiveness of these materials was then tested in a number of ways. A temperature ramp of these gels in flow ($\gamma=0.5$ s$^{-1}$; FIG. 7) as well as steady-shear rheology of these gels at elevated temperature (FIG. 8A) indicate that the mechanical response is completely unchanged by temperature. This insensitivity of the rheological properties to temperature is highly distinguishing from other reported non-covalently cross-linked systems that exhibit tremendous loss of mechanical stability with increasing temperature. As cross-linking in these other systems is strongly enthalpically driven, whereby association constants decrease significantly with increasing temperature, yielding a decrease in the density of effective crosslinks and thus a decrease in the mechanical properties. It is conceivable that the polymer-nanoparticle interactions exploited in this system are entropically driven, enabling complete stability to temperature over typical ranges.

Figure 8B:
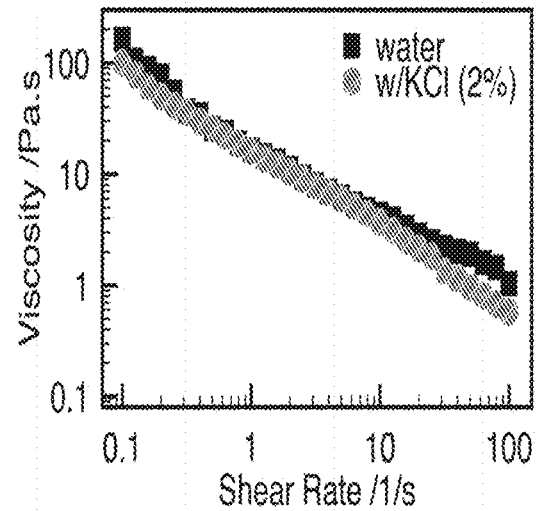
Figure 8C:
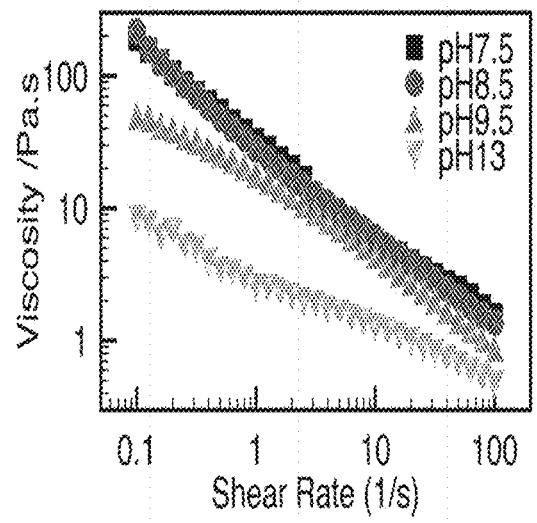
Figure 9A:
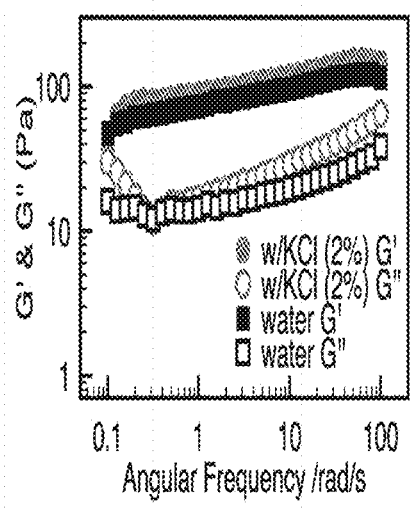
FIG. 9A-9B shows rheological properties of cellulose silica-based hydrogels prepared with KCl or water.
Figure 9B:
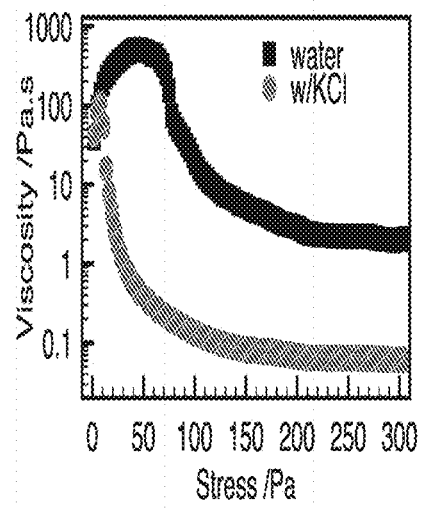

These materials are completely stabile to increased ionic strength (2% KCl; FIG. 8B), while they exhibit some pH responsiveness (FIG. 8E and FIG. 9). When the pH is increased above 9, the gels start to lose some of their integrity as the surface silanol groups on the CSPs are deprotonated above this pH.

Figure 8D:
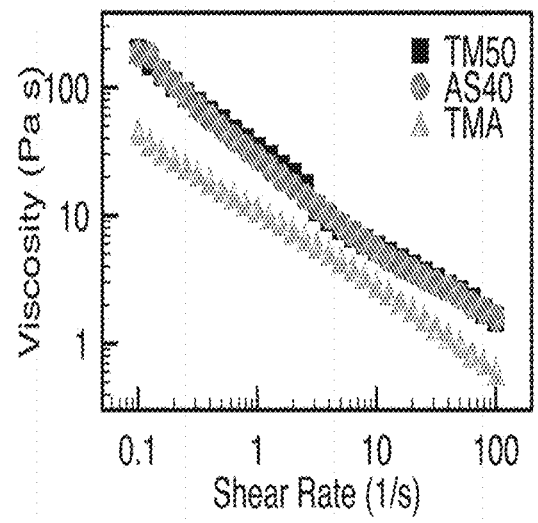
Figures 10A, 10B:
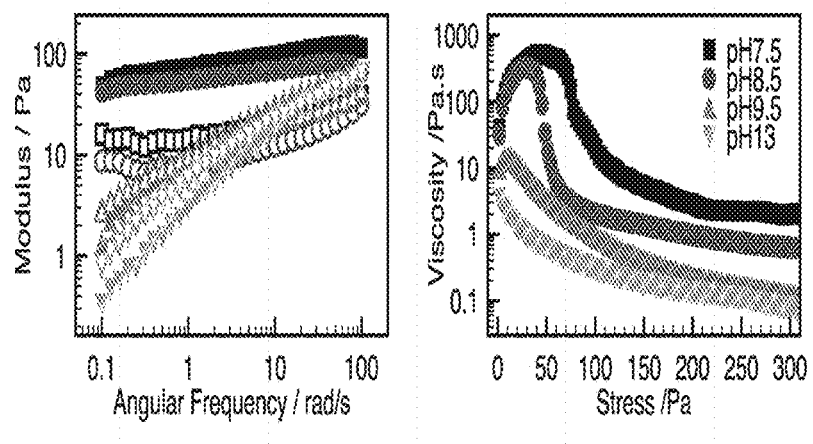
FIG. 10A shows steady-shear rheological properties and FIG. 10B shows yield-stress measurements of colloid silica-based trimeric hydrogels prepared at various pH values, comprising HEC (0.85 wt %)/MC (0.15 wt %)/CSPs (5 wt %), demonstrating the mechanical impact of alterating the pH value.
Figure 11A:
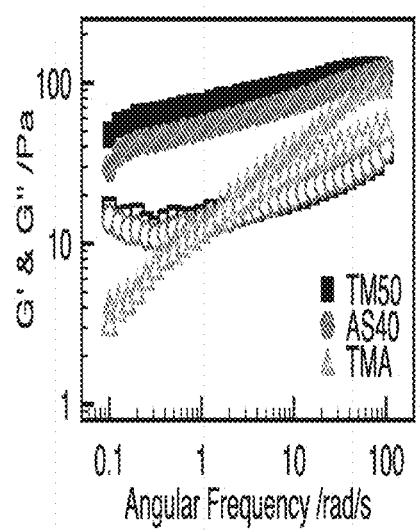
FIG. 11A shows steady-shear rheological properties and FIG. 11B shows yield-stress measurements of colloid silica-based trimeric hydrogels, comprising HEC (0.85 wt %)/MC (0.15 wt %)/CSPs (5 wt %), prepared with colloidal silica nanoparticles of identical size, but with different surface compositions or stabilizing counter-ions, demonstrating the mechanical impact of altering the colloidal silica nanoparticle. TM50 has an anionic silica surface and sodium counter-ion, AS40 has an anionic silica surface and an ammonium counter-ion, and TMA has a cationic aluminum surface and a chloride counter-ion.
Figure 11B:
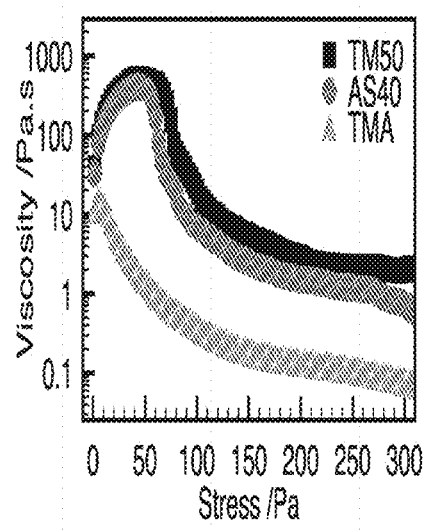
Figures 12A, 12B:
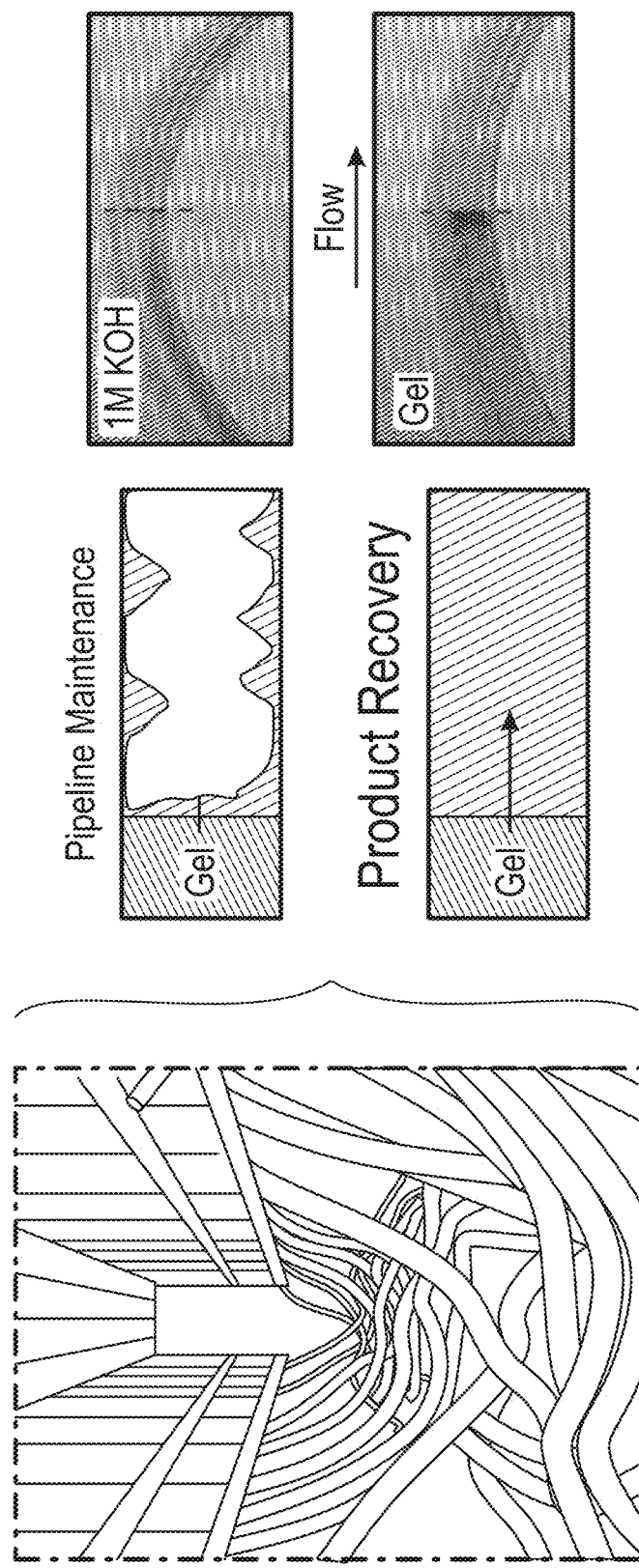
FIG. 12A-12E illustrates the principle of pipeline pigging for enhanced product recovery and more efficient pipeline maintenance.
Figure 12C:
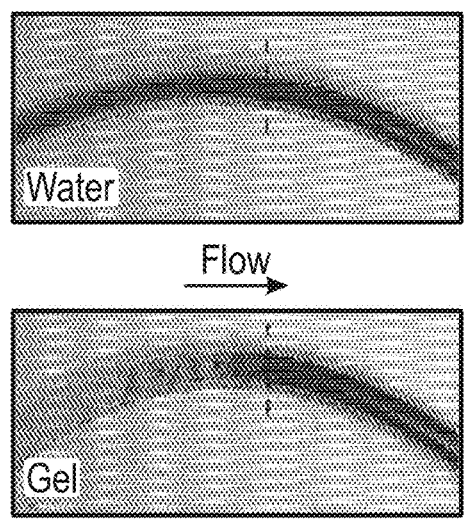
Figure 12D:
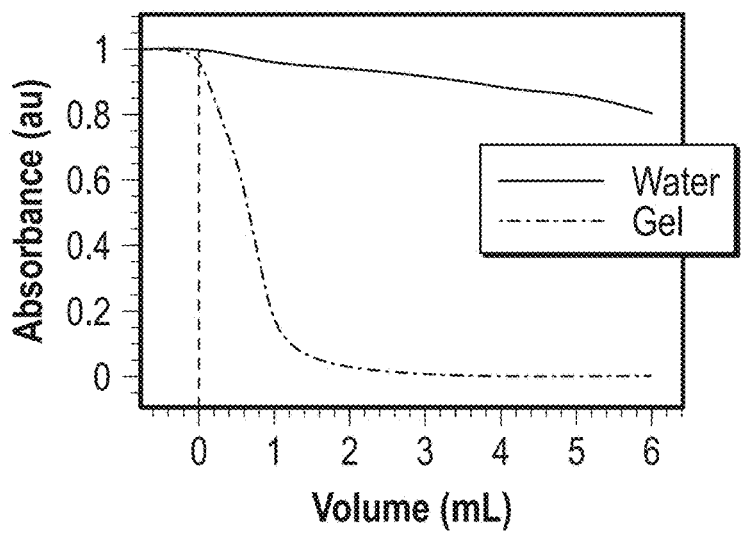
Figure 12E:
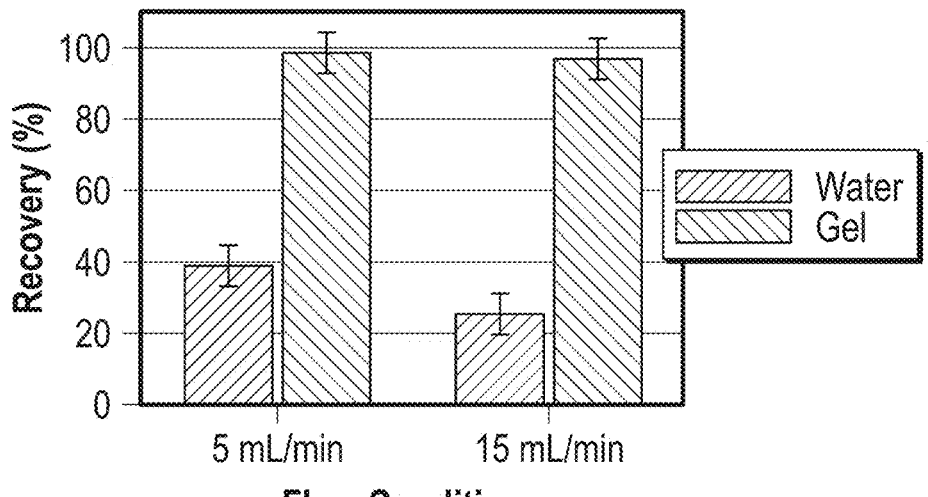
Figure 13A:
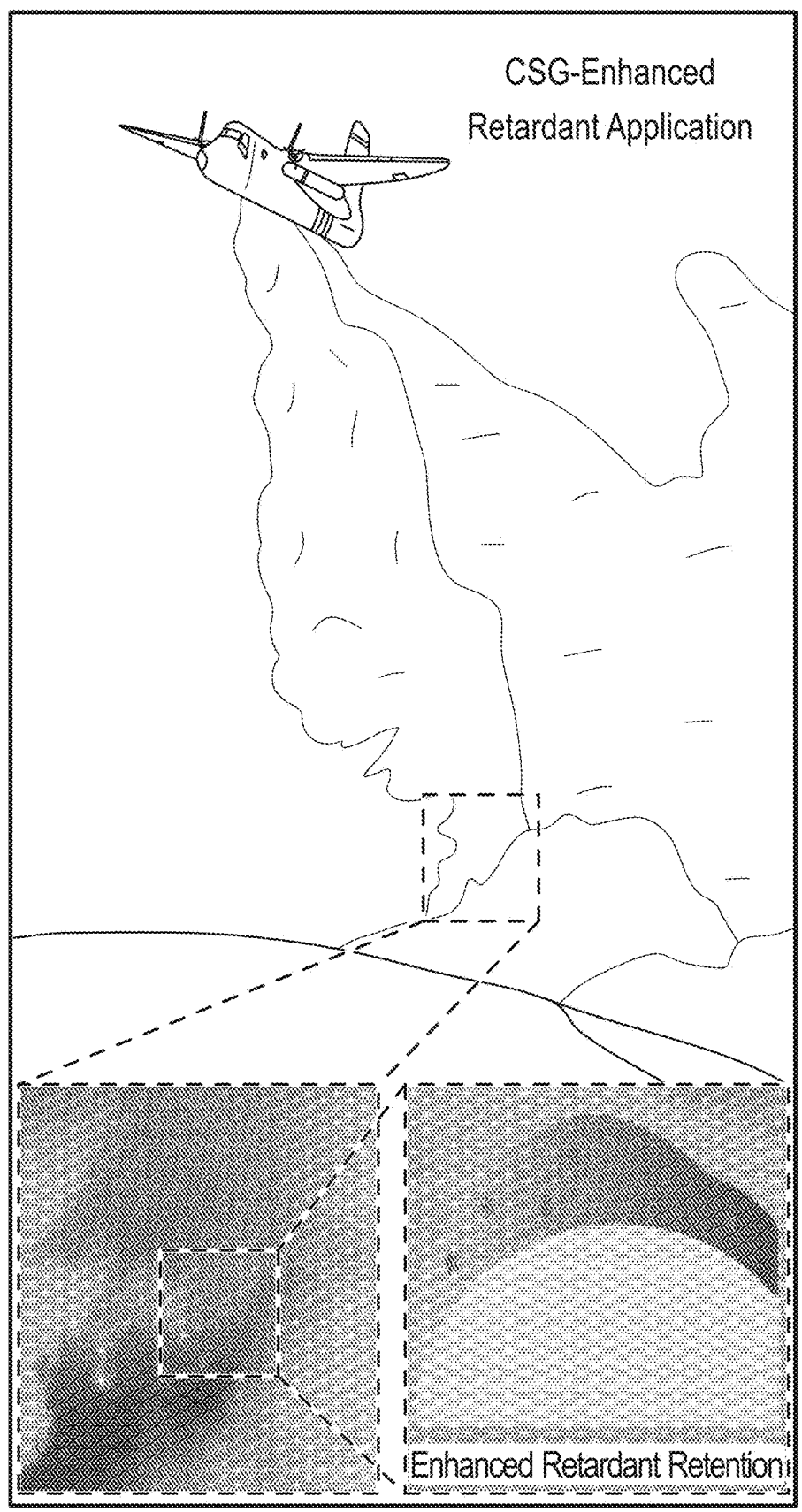
FIGS. 13A-13D illustrates the utility of cellulose silica-based trimeric hydrogels as carriers of fire-retardants.
Figure 13B:
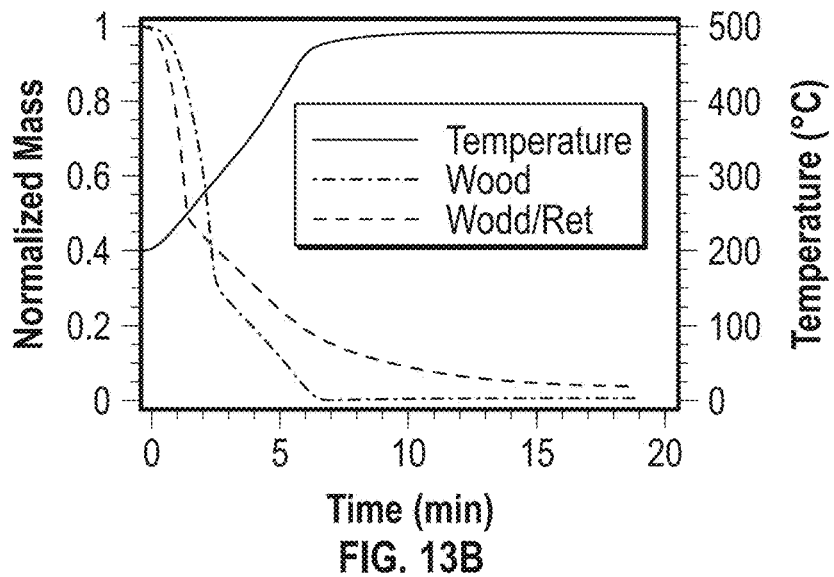
Figure 13C:
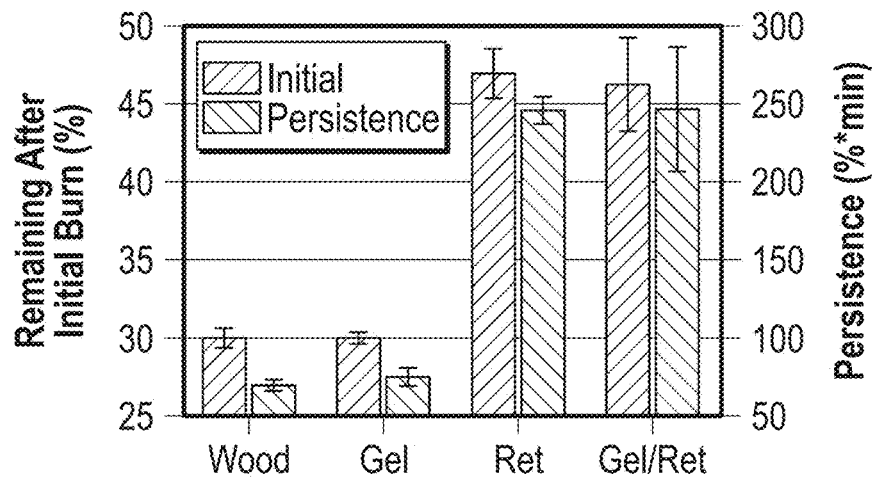
Figure 13D:
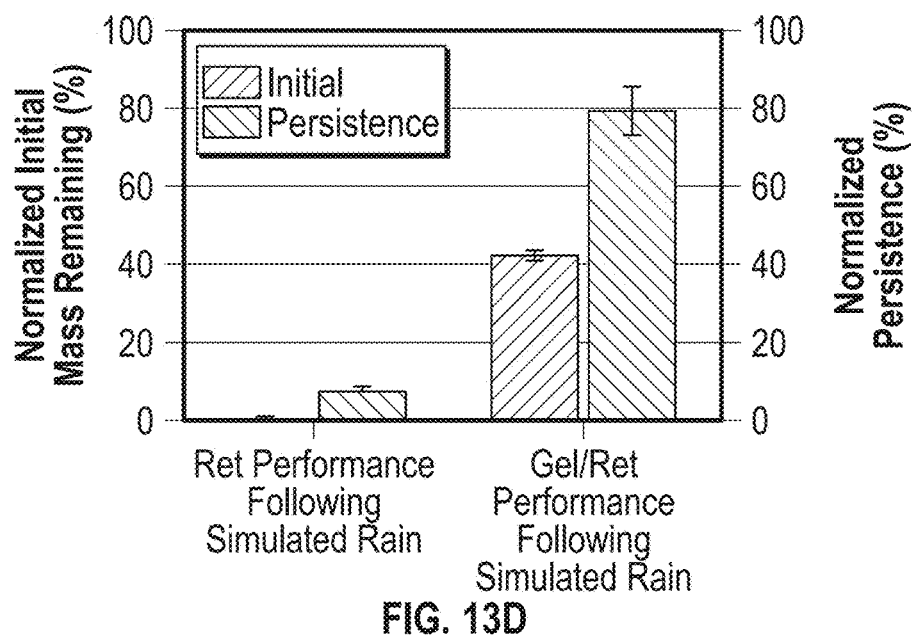
Figure 14A:
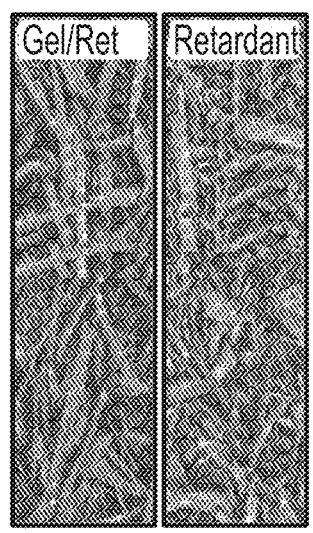
FIGS. 14A-14C illustrates how fire retardant/hydrogel-based formulations and standard retardant formulations were applied using a backpack sprayer to Chamise (greasewood) chipped to a size defined as a "one-hour" fuel. The hydrogel provided enhanced surface coverage and adherence of the retardant treatment to the fuel (FIG. 14A). Burning the treated fuel (1 kg) in a test chamber while monitoring temperature over time with type K thermocouples demonstrated that enhanced coverage through hydrogel-based application resulted in greatly enhanced performance, indicated both by longer burn duration (i.e., slower heat release) (FIGS. 14B-14C) and lower maximum temperatures (FIG. 14C).
Figure 14B:
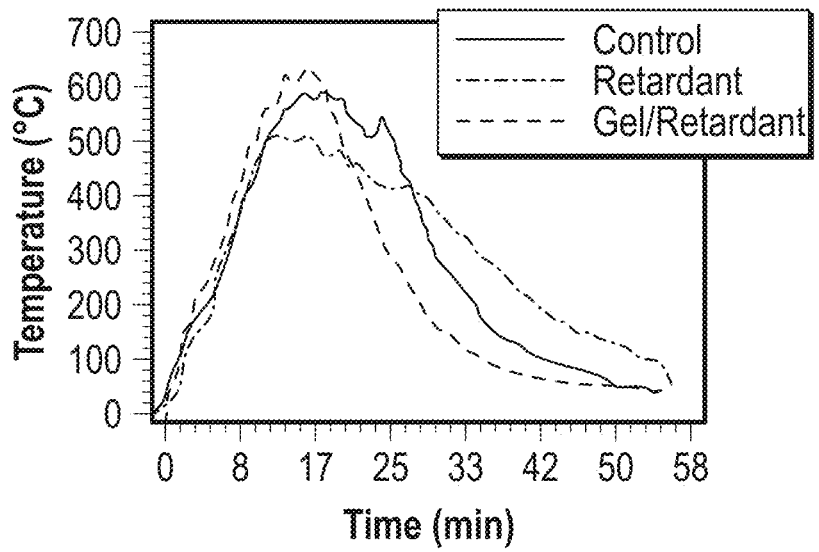
Figure 14C:
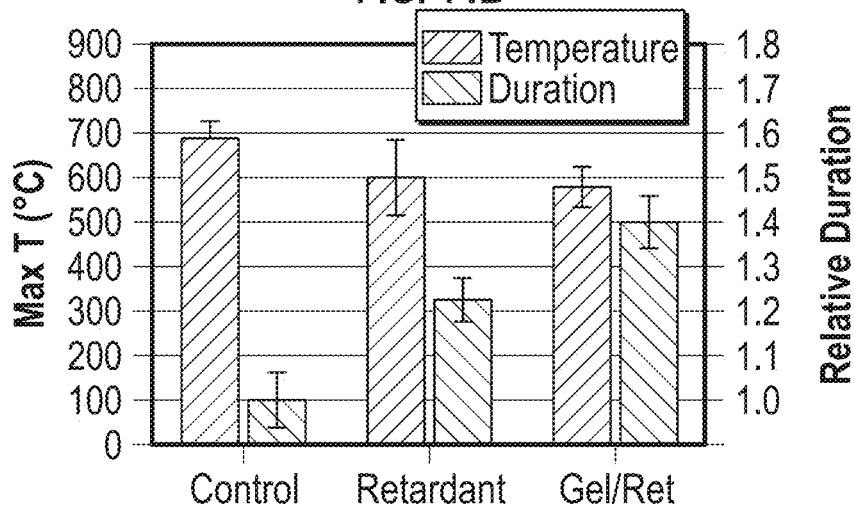
Figure 15A:
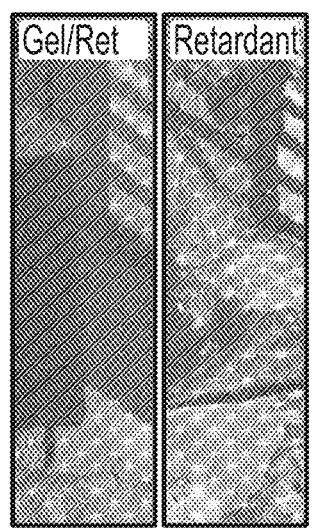
FIGS. 15A-15C illustrates a simulated rain event that corresponded to approximately 0.25" of rain-fall on fuels treated with fire retardant/hydrogel-based formulations and standard retardant formulations, respectively, using a backpack sprayer. Following the rain event, the standard retardant formulations were washed away, as evidenced by the red tinted of the run-off water FIG. 15A, while the hydrogel-based application resulted in complete retention of the retardant on the fuel, as subsequent burning in a test chamber showed. Burning these samples (1 kg) in a test chamber in the same manner, as described in the previous figure, indicated enhanced persistence of the fire retardant on the fuel throughout the rain event by longer burn duration (FIGS. 15B-15C) and lower maximum temperatures (FIG. 14C).
Figure 15B:
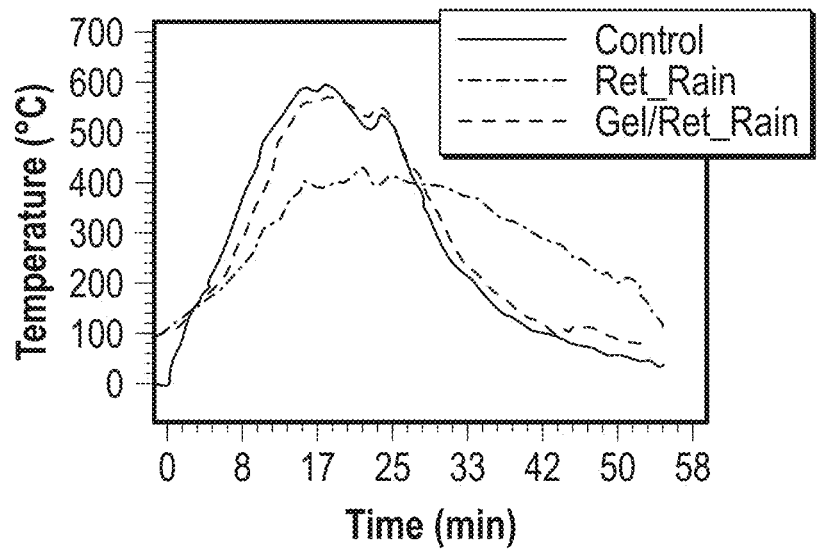
Figure 15C:
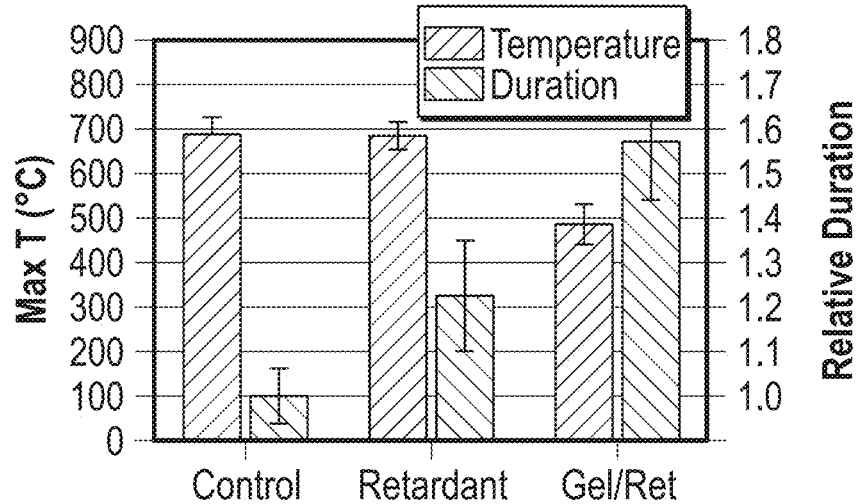

The hydrogels formed by colloidal silica nanoparticles bearing different surface chemistry (Ludox TMA) with pairs of cellulose derivatives were qualitatively screened and found to exhibit dramatically different mechanical properties. In detail, the mechanical properties of cellulose silica-based hydrogels with 3 different kinds of colloidal silica nanoparticles (Ludox TMA, Ludox TM-50 and Ludox AS-40) were investigated (FIG. 8D and FIG. 10). Ludox TM-50 and Ludox AS-40 silica nanoparticles comprise anionic silonol groups on their surface in basic solution that are stabilized by sodium ions or ammonium ions, respectively. In contrast, Ludox TMA silica nanoparticles comprise cationic alumina on their surface that is stabilized with chloride ions.

The rheological characterization shows that cellulose silica-based hydrogels formed by AS-40 and TM-50 have identical mechanical properties in all the measurements shown in both flow and oscillatory rheology. However, TMA-based materials hardly formed gels and despite having only a slightly reduced G' value, exhibited a much higher degree of fluidity. Similarly, the hydrogels with TMA-based materials had a much lower yield stress than the hydrogels formed by AS-40 and TM-50. These data corroborate that the chains of the polymers (cellulose derivatives) absorb to select colloidal silica surfaces, which leads to the trimeric hydrogel formation; the counter ions, however, do little or nothing to impact this process.

Example 2

Use of Cellulose Silica-Based Hydrogel as Carriers for Pipeline Pigging in Food and Beverage Manufacturing Industrial settings present many unique and complicated engineering challenges. Inefficiencies arise in manufacturing as large volumes of material need to be pumped from one location to another, and vast lengths of varying diameter pipe must be cleaned frequently (Tiratsoo, 1992). Applications as diverse as hydraulic fracturing and cosmetics rely on processable fluids with complex viscoelastic properties. Moreover, many products and coatings are applied through spraying, which often requires uniform application and tunable retention of solvent and/or product.

Pipeline pigging refers to the practice of using devices to perform various maintenance operations (e.g., cleaning or inspecting) on a pipeline without stopping the flow of the product in the pipeline (the name "pigging" arises from the squealing and snorting sound traditional mechanical "pigs" produce while traveling through a pipe) (Tiratsoo, 1992; Cordell & Vanzant, 2003). These processes have been used for many years to clean large diameter pipelines in the oil industry; however, the use of smaller diameter pigging systems has seen recent growth in industries handling products as diverse as paints, chemicals, and cosmetics to avoid cross-contamination and to increase product yields and reduce waste. Yet, for all of its benefits, the process is limited by the availability of materials amenable to both the product and pipeline systems at hand. For example, a pipeline cannot be "pigged" traditionally if it contains butterfly valves or reduced-bore ball valves, or comprises various sizes of piping (common in many older factories) (Cordell & Vanzant, 2003). Moreover, many standard pigging systems cannot be used with food products. Currently, most operators of batch processes in food production ensure maximum product recovery from a line by flushing the line with water (in some cases, this can sometimes be done with the next product). During these processes it is often necessary to downgrade or dump the contaminated or diluted portion of the product. Further, as many food products lead to pipeline fouling, cleaning agents (e.g., hot caustic soda solutions) are often used, which must be subjected to effluent treatment or costly waste disposal (Gesan-Guiziou et al., 2002; Merin et al., 2002; Bremer et al., 2006). Many, if not all, of these problems could be eliminated with next-generation pigging systems, which would serve to both increase production and reduce the environmental impact of diverse batch operations.

One promising approach reported recently is based on the use of a slurry of ice for pigging, which could be easily applied in the food and beverage industries (Quarini, 2002; Quarini & Shire, 2007; Quarini et al., 2010). As these ice slurries are pumpable, they can form a soft plug capable of adapting its shape to fill complex pipe architectures, enhancing produce recovery and pipeline cleaning. However, ice production, transportation and storage is expensive, energy intensive, and poorly scalable. Moreover, as ice melts rapidly when present in small particles, the distance over which an ice slurry may function as an effective "pig" is severely limited (Evans et al., 2008; Hales et al., 2014). This is particularly problematic in industries where most product movement occurs during the summer months (e.g., wine production).

Scalable and moldable cellulose silica-based trimeric hydrogels that were prepared from environmentally safe, cost-effective and renewable polysaccharide starting materials, as described in Example 1, were applied to address the particular challenge of pipeline maintenance in large-scale wine production. Large-scale wine production is highly dependent on product transfer through diverse pipeline systems during the many stages of production, including crushing of the fruit, fermentation, aging, and bottling, as shown in FIG. 5a. According to the Wine Institute, wine production in the U.S. is approaching 1 Billion gallons/year and anecdotal evidence from within the industry indicates that up to 2% of product may be lost during production.

Indeed, in large wineries, over 20 cases of wine may be lost per transfer. Besides an acceptable safety profile both for use in food products and for the environment, a viable pigging system must be tasteless, scentless, and colorless to avoid any perturbation of the product.

Cellulose Silica-Based Trimer Hydrogels are Tasteless, Scentless and Odorless

As all components of the scalable and moldable cellulose silica-based trimer hydrogels are highly pure, chemically simple, and widely utilized in food production, a blind taste test was performed with three blinded professional wine makers. For these experiments, one of three identical samples of wine was mixed with a cellulose silica-based trimer hydrogel to a concentration of approximately 1 wt % hydrogel. Three blinded professional wine makers then tested all samples of wine in an attempt to identify the sample that contained the cellulose silica-based trimer hydrogel, but none of them detected a statistically significant difference with respect to taste, scent or odor confirming that cellulose silica-based trimer hydrogels are tasteless, scentless and odorless. Consequently, selected cellulose silica-based trimer hydrogel formulations were investigated for pipeline pigging both in the recovery of product and in pipeline cleaning.

Initially, a trimeric hydrogel formulation with HEC (1.2 wt %):MC (0.3 wt %):CSP (7.5 wt %) was tested for pipeline cleaning applications. This formulation was chosen on account of its material properties (maximizing G' and minimizing tan$\delta$) and low content of solids (comprising 91% water). Laboratory-scale experiments were designed to emulate current approaches in batch processes in industrial-scale food and beverage manufacturing. A test pipe (d=½", l=24") was allowed to foul with Purple 8000 crushed-grape concentrate (10% v/v) for 1 h. Then, either KOH (1M; industry standard) or cellulose silica-based hydrogel was pumped through the pipe (at a rate of 15 mL/min) to remove the grape residue. As seen in FIG. 5B, cellulose silica-based hydrogel provides greatly enhanced scouring of the piping over the industry standard, which often requires soaking for several hours before flushing through the pipe to effectively dislodge grape residue. Aqueous solutions of Purple 8000 grape concentrate (10% v/v) were then propelled through a test pipe (d=½ ", l=24") with one pipe volume (~77 mL) of either water (consistent with industry standard practice) or cellulose silica-based hydrogel. By monitoring the absorbance of the Purple 8000 ($\lambda_{max}$=535 nm) in the eluent over time, it was possible to determine the recovery of Purple 8000 from the pipeline (using a cut-off at dilution to 80%, as shown in FIGS. 5C-5E).

Cellulose silica-based hydrogel formulations created a defined interface with the model product, allowing for greatly enhanced product recovery over the industry standard and demonstrating that these hydrogel formulations can be used with industry standard pumps (e.g., progressive cavity pumps, peristaltic pumps, or diaphragm pumps). These results establish that cellulose silica-based hydrogel formulations can serve as scalable, food-safe, environmentally benign and water-wise options for pipeline pigging in industrial scale food and beverage manufacturing.

Example 3

Use of Cellulose Silica-Based Trimeric Hydrogels as Carriers of Fire Retardants for Enhanced Fire Retardant Performance and Rainfastness to Prevent Wildland Fires by Pretreating High-Risk Areas and to Directly Fight Wildland Fires According to the National Interagency Fire Center (NIFC), wildland fires in the U.S. destroy almost 10 million acres/year and the cost of fighting wildland fires in the U.S. is estimated to be roughly $2 B annually. The NIFC is a federal organization coordinating the efforts of multiple federal agencies, including the Bureau of Land Management, Bureau of Indian Affairs, US Fire Service, US National Park Service, US Fish & Wildlife Service, and the US National Association of State Foresters.

Fire retardants, typically comprising ammonium polyphosphates in aqueous formulation, constitute a primary tactical resource in fighting wildland fires, with over 30 million gallons pumped annually in the US alone (Gimenez et al., 2004; Yount, 2015). Yet, their tactical utility is severely limited by their current formulations which must often be dropped from low altitudes on account of drift or rapid evaporation while falling, or are incapable of retaining these retardants at the target site.

Another class of highly effective retardants are aqueous film forming foams, which comprise perfluorinated surfactants, the primary fire extinguishing chemical driving their performance (Kissa, 1994). However, wastewater from the use of these foams and its treatment have been the focus of rigorous investigative studies as fluorinated surfactants have been found to contaminate groundwater around the site of application and have emerged as primary environmental contaminants due to their environmental persistence, potential for bioaccumulation, and toxicity (Kissa, 1994; Moody & Field, 2000; Moody et al., 2002; 2003; Hu et al., 2016). The use of these foams is therefore highly restricted.

Furthermore, "water-enhancing gels," which are aqueous dispersions of super-absorbent polymers similar to the materials used in disposable diapers, have demonstrated the capacity to extend water's effectiveness in preventing fires from starting and/or spreading (Schroeder, 2005; 2006a; 2006b). These water-enhancing gel materials, however, are non-degradable and petroleum-derived, posing significant environmental concerns and limiting their applicability.

Cellulose Silica-Based Trimeric Hydrogels Enhance Fire Retardant Performance and Fire Retardant's Rainfastness Scalable and moldable cellulose silica-based trimeric hydrogels that can be prepared from environmentally safe, cost-effective and renewable polysaccharide starting materials present a unique solution to these important industrial and environmental challenges and limitations because they are capable of imparting enhanced drop capabilities such as reduced drift, greater canopy penetration, and the potential to be dropped from greater altitudes, along with the ability to retain ammonium polyphosphates at the target site, which makes cellulose silica-based hydrogel carriers more effective and safer tactical approaches to fighting wildland fires than the presently used methods. Furthermore, enhanced retention of fire retardants with cellulose silica-based hydrogel carriers would enable application at sites of particularly high fire danger (e.g., roadsides or targets for lightning strikes), potentially preventing a vast number of wildland fires from starting in the first place.

Select cellulose silica-based hydrogel formulations (HEC (0.32 wt %):MC (0.08 wt %):CSP (2 wt %)) were formulated with Phos-Chek LC95A, an ammonium polyphosphate retardant that is typically dispersed in water. Phos-Chek LC95 is the most commonly used fire retardant in the US with approximately 15 million gallons pumped annually (Yount, 2015).

For sprayable formulations, cellulose silica-based trimer hydrogel preparations with the same component stoichiometry as above were prepared, but at a lower concentration so that the hydrogel preparations could be sprayed like standard aqueous formulations of the Phos-Chek LC95 fire retardant, but that the hydrogel preparations yet would have the potential to provide better canopy penetration and substantially enhanced persistence at the site of application, properties that are critical for fire prevention in high-risk areas.

Although current fire retardant formulations include small amounts of thickening agents (e.g., Palygorskite clay), their efficacy is completely neutralized by subsequent drops of water (limiting tactical approaches to directly fighting fires) or even by minimal rainfall (precluding preemptive use).

In the investigation of cellulose silica-based trimer hydrogel preparations as carriers for fire retardants, pinewood flour, which is a model high-surface-area to volume fuel, was treated with the hydrogel preparations in various ways, and thermal gravimetric analysis (TGA) was performed to characterize mass loss upon burning, as shown in FIG. 13*b*. TGA was performed on account of its prevalence in studies regarding material ignition and decomposition processes as well as quantification of flame retardant performance (Drevelle et al., 2005; Gu et al., 2007).

Both the mass remaining after the initial burn and the persistence of mass over time for untreated wood was determined as well as for wood treated with hydrogel alone, for wood treated with aqueous retardant, and for wood treated with retardant-containing hydrogel, as shown in FIG. 13*c*. When comparing untreated wood and wood treated with standard aqueous retardant formulations, it is apparent that the fire retardant decreases both the initial mass loss and inhibits subsequent mass loss. The addition of hydrogel in either case did not significantly alter the performance of the retardant.

However, when wood samples treated with standard aqueous retardant formulation and retardant-containing hydrogel formulations were subjected to simulated rainfall, their subsequent performances differed dramatically, as shown in FIG. 13*d*. To simplify identification of the performance of the treatments (standard aqueous retardant formulation versus retardant-containing hydrogel formulations) following simulated rainfall, the TGA data were normalized to reflect the response of wood alone (yielding a performance rating of 0%) and wood freshly treated with standard aqueous retardant formulation (yielding a performance rating of 100%).

When fire retardant-containing cellulose silica-based hydrogel was applied to "one-hour" fuel, as illustrated in FIG. 14A, the fire retardant-gel combination enhanced adherence of the retardant treatment to the fuel which resulted in a 95% surface coverage, while the surface coverage of standard retardant treatment was only 80%. When the treated "one-hour" fuel was burned in a test chamber, the enhanced surface coverage and enhanced adherence of the retardant when applied as fire retardant-gel led to longer burn duration (FIGS. 14B-14C), i.e. slower heat release, and lower maximum temperatures (FIG. 14C).

To further test the enhanced rainfastness of fire retardant-hydrogel preparations, a rain event was simulated that corresponded to approximately 0.25" of rain-fall on fuels treated with retardant/hydrogel and standard retardant formulations, respectively, using a backpack sprayer. Following the rain event, the standard retardant formulations were washed away, as evidenced by the red tinted of the run-off water (FIG. 15*a*), while the gel-based application resulted in complete retention of the retardant on the fuel, as subsequent burning in a test chamber showed. Burning these samples (1 kg) in a test chamber indicated enhanced persistence of the fire retardant on the fuel throughout the rain event by longer burn duration (FIG. 15*b/c*) and lower maximum temperatures (FIG. 15*c*).

These results clearly show that hydrogel formulations retain the fire retardants on the fuel throughout the simulated rainfall, while standard formulations are washed away, losing their performance, as shown by a loss of functional performance following a subsequent burn (FIG. 15*c*). In contrast, the fire retardant-hydrogel-based application resulted in complete retention of the retardant on the fuels, which led to complete maintenance of retardant performance. While these gel materials can be formulated to persist for several months in the environment, even through small rain events, their physical nature will allow them to completely biodegrade in the environment after the fire season. Therefore, prophylactic treatment of areas at high-risk for fire starts (e.g., roadsides) with fire-retardant-hydrogel formulations will be instrumental in preventing fires from starting in the first place.

Fire-retardant-hydrogel formulations have, thus, the potential to provide dramatically enhanced retardant persistence at the site of application while allowing for facile application through standard spray or drop approaches.

Example 4

Use of Cellulose Silica-Based Trimeric Hydrogels as Carriers of Fertilizers and Pesticides Cellulose silica-based trimeric hydrogel formulations are not only suited to serve as easily applicable and well-retaining, i.e. not quickly washed-away, carriers for the delivery of fire retardants, as described in Example 3, but also suited to serve as such carriers for the controlled delivery of fertilizers such as ammonium polyphosphates (which was described in Example 3 as common ingredient in fire retardants) and pesticides.

Since, as explained in Example 3, such hydrogel formulations are easily applicable as sprayable carriers, but not readily washed away by light rain, they can be applied onto crops and other materials with enhanced surface coverage and enhanced fertilizing and pesticidal performance, respectively. Since such hydrogel formulations are not readily washed away by light rain, their use as carriers for pesticides and fertilizers will result in less groundwater contamination through washed-away pesticides and fertilizers.

Although the foregoing invention and its embodiments have been described in some detail by way of illustration and example for purposes of clarity of understanding, it is readily apparent to those of ordinary skill in the art in light of the teachings of this invention that certain changes and modifications may be made thereto without departing from the spirit or scope of the appended claims. Accordingly, the preceding merely illustrates the principles of the invention. It will be appreciated that those skilled in the art will be able to devise various arrangements which, although not explicitly described or shown herein, embody the principles of the invention and are included within its spirit and scope.

REFERENCES

Appel E A, del Barrio J, Loh X J, & Scherman O A (2012a) Supramolecular Polymeric Hydrogels. Chem. Soc. Rev. 41:6195-6214.

Appel E A, et al. (2015a) Self-assembled hydrogels utilizing polymer-nanoparticle interactions. Nature Commun. 6:6295.

Appel E A, et al. (2015b) Exploiting Electrostatic Interactions in Polymer-Nanoparticle Hydrogels. Acs Macro Lett 4(8):848-852.

Bergna H E & Roberts W O (2005) Colloidal Silica: Fundamentals and Applications (Taylor & Francis Group, New York).

Cordell J & Vanzant H (2003) The Pipeline Pigging Handbook (Clarion Technical Publishers and Scientific Surveys Ltd.) 3rd Ed.

Drevelle C, et al. (2005) Thermal and fire behaviour of ammonium polyphosphate/acrylic coated cotton/PESFR fabric. Polym Degrad Stabil 88(1):130-137.

Evans T S, Quarini G L, & Shire G S F (2008) Investigation into the transportation and melting of thick ice slurries in pipes. Int. J Refrig 31(1):145-151.

Gesan-Guiziou G, Boyaval E, & Daufin G (2002) Nanofiltration for the recovery of caustic cleaning-in-place solutions: robustness towards large variations of composition. J Dairy Res 69(4):633-643.

Merin U, Gesan-Guiziou G, Boyaval E, & Daufin G (2002) Cleaning-in-place in the dairy industry: criteria for reuse of caustic (NaOH) solutions. Lait 82(3):357-366.

Bremer P J, Fillery S, & McQuillan A J (2006) Laboratory scale Clean-In-Place (CIP) studies on the effectiveness of different caustic and acid wash steps on the removal of dairy biofilms. Int J Food Microbiol 106(3):254-262.

Gimenez A, Pastor E, Zarate L, Planas E, & Arnaldos J (2004) Long-term forest fire retardants: a review of quality, effectiveness, application and environmental considerations. Int J Wildland Fire 13(1):1-15.

Gu J W, Zhang G C, Dong S L, Zhang Q Y, & Kong J (2007) Study on preparation and fire-retardant mechanism analysis of intumescent flame-retardant coatings. Surf Coat Tech 201(18):7835-7841.

Hales A, et al. (2014) Ice fraction measurement of ice slurries through electromagnetic attenuation. Int J Refrig 47:98-104.

Hu X C, et al. (2016) Detection of Poly- and Perfluoroalkyl Substances (PFASs) in U.S. Drinking Water Linked to Industrial Sites, Military Fire Training Areas, and Wastewater Treatment Plants. Environ. Sci. Technol. Lett. article.

Kapsabelis S & Prestidge C A (2000) Adsorption of ethyl(hydroxyethyl)cellulose onto silica particles: The role of surface chemistry and temperature. J Colloid Interf Sci 228(2):297-305.

Kissa E (1994) Fluorinated surfactants : synthesis, properties, applications (M. Dekker, New York) pp vii, 469 p.

Moody C A & Field J A (2000) Perfluorinated surfactants and the environmental implications of their use in firefighting foams. Environ Sci Technol 34(18):3864-3870.

Moody C A, Martin J W, Kwan W C, Muir D C G, & Mabury S C (2002) Monitoring perfluorinated surfactants in biota and surface water samples following an accidental release of fire-fighting foam into Etobicoke Creek. Environ Sci Technol 36(4):545-551.

Moody C A, Hebert G N, Strauss S H, & Field J A (2003) Occurrence and persistence of perfluorooctanesulfonate and other perfluorinated surfactants in groundwater at a fire-training area at Wurtsmith Air Force Base, Michigan, USA. J Environ Monitor 5(2):341-345.

Quarini J (2002) Ice-pigging to reduce and remove fouling and to achieve clean-in-place. Appl Therm Eng 22(7): 747-753.

Quarini J & Shire S (2007) A review of fluid-driven pipeline pigs and their applications. P I Mech Eng E-J Pro 221(E1): 1-10.

Quarini G, et al. (2010) Investigation and development of an innovative pigging technique for the water-supply industry. P I Mech Eng E-J Pro 224(E2):79-89.

Rodell C B, et al. (2015) Shear-Thinning Supramolecular Hydrogels with Secondary Autonomous Covalent Crosslinking to Modulate Viscoelastic Properties. Adv Funct Mater 25(4):636-644.

Rose S, et al. (2014) Nanoparticle Solutions as Adhesives for Gels and Biological Tissues. Nature 505:382-385.

Schroeder D (2005) Can Fire Suppressant Gels Protect Log Decks? A Case Study to Test the Concept. (Vancouver, Canada).

Schroeder D (2006a) Can Fire Suppressant Gels Protect Log Decks? Part III—Two case studies to test gel effectiveness against radiant and convective heat transfer. (Vancouver, Canada).

Schroeder D (2006b) Effectiveness of Forest Fuel Management: A Crown Fire Case Study in the Northwest Territories, Canada. (Vancouver, Canada).

Tamesue S, et al. (2013) Linear versus Dendritic Molecular Binders for Hydrogel Network Formation with Clay Nanosheets: Studies with ABA Triblock Copolyethers Carrying Guanidinium Ion Pendants. Journal of the American Chemical Society 135 (41): 15650-15655.

Tiratsoo J N H (1992) Pipeline pigging technology (Gulf Pub. Co., Houston) 2nd Ed, 460 p.

Wang Q, et al. (2010) High-Water-Content Mouldable Hydrogels by Mixing Clay and a Dendritic Molecular Binder. Nature 463(7279):339-343.

Yount B (2015) Summary of National Retardant Use for 2015.

What is claimed is:

1. A method of retarding the effect or degree of a fire comprising:
    applying a fire-retardant hydrogel preparation to a fire-prone area wherein the fire-retardant hydrogel preparation comprises an ammonium polyphosphate retardant and hydroxyethylcellulose, methylcellulose, and colloidal silica particles, and wherein the hydroxyethylcellulose and methylcellulose are cross-linked by the colloidal silica particles to form a non-covalently cross-linked hydrogel.

2. The method of claim 1 wherein the ratio of hydroxyethylcellulose and methylcellulose to the colloidal silica particles is 1:5.

3. The method of claim 1 wherein the hydrogel preparation is configured to be shear-thinning and self-healing.

4. The method of claim 1, wherein the hydrogel preparation is formulated to maintain controllable mechanical properties between temperatures of 20 to 70 degree Celsius.

5. The method of claim 1 wherein the hydrogel preparation has retention at the fire-prone area even under conditions of rain.

6. The method of claim 1 wherein the hydrogel preparation is biodegradable.

7. The method of claim 1 wherein the hydrogel preparation is formulated to persist at the fire-prone area until at least 0.25" of cumulative rainfall.

8. The method of claim 1 wherein the hydrogel preparation is formulated as a spray.

* * * * *